(12) United States Patent
Bidlingmeyer et al.

(10) Patent No.: US 7,125,492 B2
(45) Date of Patent: Oct. 24, 2006

(54) ADDITIVES FOR REVERSED-PHASE HPLC MOBILE PHASES

(75) Inventors: Brian Bidlingmeyer, Frazer, PA (US); Qunjie Wang, Hockessin, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/621,953

(22) Filed: Jul. 17, 2003

(65) Prior Publication Data

US 2005/0011836 A1    Jan. 20, 2005

(51) Int. Cl.
    B01D 15/08    (2006.01)
(52) U.S. Cl. ............ 210/635; 210/656; 210/198.2
(58) Field of Classification Search .......... 210/635, 210/656, 198.2, 659
    See application file for complete search history.

(56) References Cited

U.S. PATENT DOCUMENTS

| | | | |
|---|---|---|---|
| 4,600,646 A | 7/1986 | Stout | |
| 4,675,383 A | 6/1987 | Bohlen et al. | |
| 4,816,159 A | 3/1989 | Khosah et al. | |
| 4,871,711 A | 10/1989 | Martin et al. | |
| 4,909,941 A | 3/1990 | Poll et al. | |
| 4,929,589 A | 5/1990 | Martin et al. | |
| 4,994,429 A | 2/1991 | Wieserman et al. | |
| 5,037,795 A | 8/1991 | Wieserman et al. | |
| 5,200,069 A * | 4/1993 | Lin | 210/198.2 |
| 5,207,914 A * | 5/1993 | Lin | 210/635 |
| 5,246,588 A | 9/1993 | Tonelli et al. | |
| 5,262,057 A | 11/1993 | Tonelli et al. | |
| 5,322,627 A * | 6/1994 | Berger et al. | 210/656 |
| 5,338,454 A * | 8/1994 | Duff | 210/635 |
| 5,585,236 A * | 12/1996 | Bonn et al. | 435/5 |
| 5,772,889 A | 6/1998 | Gjerde et al. | |
| 5,795,976 A | 8/1998 | Oefner et al. | |
| 5,824,225 A | 10/1998 | Powell et al. | |
| 5,968,368 A | 10/1999 | Powell et al. | |
| 6,024,878 A | 2/2000 | Gjerde et al. | |
| 6,056,877 A | 5/2000 | Gjerde et al. | |
| 6,210,885 B1 | 4/2001 | Gjerde et al. | |
| 6,287,822 B1 | 9/2001 | Gjerde et al. | |
| 6,342,161 B1 | 1/2002 | Gjerde et al. | |
| 6,486,309 B1 | 11/2002 | Gerber et al. | |
| 6,488,855 B1 | 12/2002 | Taylor et al. | |
| 6,521,123 B1 * | 2/2003 | Gjerde et al. | 210/198.2 |
| 6,524,480 B1 * | 2/2003 | Gjerde et al. | 210/635 |
| 2001/0023848 A1 | 9/2001 | Gjerde et al. | |
| 2002/0003109 A1 | 1/2002 | Gjerde et al. | |
| 2002/0038786 A1 | 4/2002 | Gjerde et al. | |
| 2002/0137037 A1 | 9/2002 | Hornby et al. | |
| 2002/0158017 A1 | 10/2002 | Gjerde et al. | |
| 2002/0185441 A1 * | 12/2002 | Gjerde et al. | 210/656 |

OTHER PUBLICATIONS

A Review of Waters' New Hybrid Particle Technology and Its Use in High Performance Liquid Chromatography (HPLC), Waters Corporation 1999 pp. 1-4.*

(Continued)

Primary Examiner—Ernest G. Therkorn

(57) ABSTRACT

The present invention provides silica-based reversed-phase HPLC methods that lead to higher retention of the analytes in the column and longer column lifetimes than usually observed under medium to high pH aqueous mobile phase conditions. The inventive methods comprise eluting the HPLC column using an aqueous mobile phase comprising at least one fluorinated additive. Preferred additives are polyfluorinated alcohols such as 2,2,2-trifluoroethanol and 1,1,1,3,3,3-hexafluoroisopropanol. The methods of the present invention may be used for analyzing, separating, purifying, and/or isolating small organic molecules, natural products, as well as biomolecules such as polypeptides, oligonucleotides and polynucleotides (e.g., DNA fragments).

26 Claims, 4 Drawing Sheets

OTHER PUBLICATIONS

Sander, Critical Reviews in Analytical Chemistry 1987, 18:299-415.*

Anderson, et al., "Characterization of Detergent-Solubilized Sarcoplasmic Reticulum Ca2+ __ATPase by High-Performance Liquid Chromatography", Biochemistry, 25: 6439-6447, 1986.

Apffel, et al., "Analysis of Oligonucleotides by HPLC-Electrospray Ionization Mass Spectrometry", Anal. Chem. 69: 1320-1325, 1997.

Ashraf-Khorassani, et al., "Packed Column Supercritical Fluid Chromatography Using Deactivated Stationary Phases", Anal. Chem. 60: 1529-1533, 1988.

Atwood, et al., "Improvements in Liquid Chromatography Column Life and Method Flexibility by Saturating the Mobile Phase with Silica", Journal of Chromatography, 171: 190-115, 1979.

Azarani, et al., "RNA Analysis by Ion-Pair Reversed-Phase High Performance Liquid Chromatography", Nucleic Acids Research, 29(2): 1-11, 2001.

Chen, et al., "Insertion of Fluoralkenes into Activated C-H Bonds for the Preparation of Polyfluorinated Sulfanes, Alcohols, and Acyclic and Cyclic Ethers", Inorg. Chem. 35: 6676-6681, 1996.

Chong, et al., "Differential Screening and Mass Mapping of Proteins from Premallgnant and Cancer Cell Lines Using Nonporous Reversed-Phase HPLC Coupled with Mass Spectrometric Analysis", Anal. Chem. 73: 1219-1227, 2001.

Cox, G., "The Influence of Silica Structure on Reversed-Phase Retention", Journal of Chromatography A, 656: 353-367, 1993.

Darling, et al., "Rapid Purification of an RNA Tumor Virus and Proteins by High-Performance Steric Exclusion Chromatography on Porous Glass Bead Columns", Journal of Chromatography, 131: 383, 390, 1977.

Dorsey, et al., "Retention Mechanisms of Bonded-Phase Liquid Chromatoraphy", Analytical Chemistry, 66(17): 857-867.

Engelhardt, et al., "Sample Size and Retention Values in High-Performance Liquid Chromatography of Biological and Synthetic Polymers", Journal of Chromatography, 458: 79-92, 1988.

Gilar, M., "Analysis and Purification of Synthetic Oligonucleotides by Reversed-Phase High-Performance Liquid Chromatography with Photodiode Array and Mass Spectrometry Detection" Analytical Biochemistry, 298: 196-206, 2001.

Hecker, et al., "Optimization of Cloning Efficacy by Pre-Cloning DNA Fragment Analysis", BioTechniques, 26: 216-222, 1999.

Hoogendoorn, et al., "Genotyping Single Nucleotide Polymorphisms by Primer Extension and High Performance Liquid Chromography", Hum Genet, 104:89-93, 1999.

Horvath, et al., "Liquid Chromography of Ionogenic Substances with Nonpolar Stationary Phases", Analytical Chemistry, 49(1): 142-158, 1977.

Huber, et al., "High-Resolution Liquid Chromatography of Oligonucleotides on Nonporous Alklated Styrene-Divinylbenzene Copolymers" Analytical Biochemistry, 212: 351-358, 1993.

Huber, et al., "Analysis of Nucleic Acids by Capillary Ion-Pair Reversed-Phase HPLC Coupled to Negative-Ion Electrospray Ionization Mass Spectrometry"Anal. Chem. 71:3730-3739, 1999.

Huber, et al., "Rapid and Accurate Sizing of DNA Fragments by Ion-Pair Chromatography on Alkylated Nonporous Poly(Styrene-Divinylbenzene) Particles", Anal. Chem. 67: 578-585, 1995.

Inchauspe, et al., "Mechanism of Selectivity in Ion-Pair High-Performance Liquid Chromatography of A minoglycoside Antibiotics using Perfluorinated Pairings Ions", Journal of Chromatography, 404: 53-66, 1987.

Kawasaki, et al., "Production and Separation of Peptides from Proteins Stained with Coomassie Brilliant Blue R-250 after Separation by Sodium Dodecyl Sulfate-Polyacrylamide Gel Electrophoresis", Analytical Biochemistry, 191: 332-336, 1990.

Kirkland, et al., "Stability of Silica-Based, Endcapped Columns with pH 7 and 11 Mobile Phases for Reversed-Phase High-Performance Liquid Chromatography", Journal of Chromatography A, 762: 97-112, 1997.

Kirkland, et al., "Reversed-Phase High-Performance Liquid Chromatography of Basic Compuonds at pH 11 with Silica-Based Column Packings", Journal of Chromatography A, 797: 111-120, 1998.

Kirkland, et al., "High pH Mobile Phase Effects on Silica-Based Reversed-Phase High-Performance Liquid Chromatographic Columns", Journal of Chromatography A, 691: 3-19, 1995.

Kirkland, et al., "Synthesis and Characterization of Highly Stable Bonded for High-Performance Liquid Chromatography Column Packings", Anal. Chem. 61: 2-11, 1989.

Kohler, et al., "Improved Silica-Based Column Packings for High-Performance Liquid Chromatography", Journal of Chromatography, 385: 125-150, 1987.

Marshall, et al., "Variable Reactivity in the Chemical Modification of Silica, Effects of Initial Deactivation on High-Performance Liquid Chromatographic Performance", Journal of Chromatography, 361: 71-82, 1986.

Myers, P., "Will Combinatorial Chemistry Deliver Real Medicines?", Current Opinion in Biotechnology, 8:701-707, 1997.

Nilsson, et al., "Identification of Protein Vaccine Candidates from Helicobacter Pylori Using a Preparative Two-Dimensional Electrophoretic Procedure and Mass Spectrometry", Anal. Chem. 72: 2148-2153, 2000.

O'Donovan, et al., "Blind Analysis of Denaturing High-Performance Liquid Chromatography as a Tool for Mutation", Genomics, 52: 44-49, 1998.

Schomburg, et al., "Immobilization of Stationary Liquids in Reversed-And Normal-Phase Liquid Chromatography", "Production and Testing of Materials for Bonded-Phase Chromatography", Journal of Chromatography, 282: 27-39, 1983.

Waddell, et al., "The Nature of Organosilane to Silica-Surface Bonding", J. Am. Chem. Soc., 103: 5303-5307, 1981.

Wehrli, et al., "Influence of Organic Based on the Stability and Separation Properties of Reversed-Phase Chemically Bonded Silica Gels", Journal of Chromatography, 149: 199-210, 1978.

Wirth, et al., "Horizontal Polymerization of Mixed Trifunctional Silanes on Silica. 2. Application to Chromatographic Silica Gel", Anal. Chem. 65: 822-826, 1993.

* cited by examiner beginning

After 62 hours

SEQUENCE LISTING

```
<160> NUMBER OF SEQ ID NOS: 2

<210> SEQ ID NO 1
<211> LENGTH: 23
<212> TYPE: DNA
<213> ORGANISM: human

<400> SEQUENCE: 1
cttctctgac actgacacgt ggc                                               23

<210> SEQ ID NO 2
<211> LENGTH: 25
<212> TYPE: DNA
<213> ORGANISM: human

<400> SEQUENCE: 2
accttctctg acactgacac gtggc                                             25
```

ADDITIVES FOR REVERSED-PHASE HPLC MOBILE PHASES

BACKGROUND OF THE INVENTION

High-Performance Liquid Chromatography (HPLC) is one of the most widely used separation techniques (J. G. Dorsey et al., Anal. Chem. 1998, 70: 591–644); and its applications range from industrial preparation to trace level detection. The popularity of HPLC stems from its ability to separate a large variety of analytes, including organics, inorganics and biomaterials with low to high molecular weights, and with different degrees of polarity, hydrophobicity, acidity, and ionization (J. Swadesh, *HPLC. Practical and Industrial Applications*, CRC Press, Boca Raton, 2001; J. S. Fritz, *Ion Chromatography*, Wiley-VCH, Weinheim, 2000). The development of highly sophisticated HPLC procedures has provided a sensitivity that allows researchers to separate enantiomers (A. Satinder, *Chiral Separations by Chromatography*, Oxford University Press, Washington, D.C., 2000) and even isotopes; to detect mutations in DNA fragments; and to achieve resolution of very similar polypeptides that differ by a single amino acid residue. The vast majority of biomedical and environmental analyses are currently performed by HPLC; and in the pharmaceutical industry, where it is the premier analytical technique, HPLC is used in all phases of drug discovery, development, and quality control.

Chromatography may be defined as the separation of analyte molecules based on their differing affinities for distinct phases in relative motion. Essentially, in HPLC, components of a sample mixture are carried through a solid stationary phase by the flow of a liquid mobile phase, that is pumped under controlled conditions of high pressure. The stationary phase, which is composed of a packed bed of finely divided beads or particles contained within a chromatography column, acts as a retentive media and differentially retards the migration of the analytes through the column so that the individual components of the mixture are gradually separated from one another and ultimately exit the column at different time points of the chromatographic run.

Successful chromatography requires a proper balance of the intermolecular forces between the analyte, the mobile phase, and the stationary phase. In HPLC, both the mobile phase and stationary phase may be varied to alter the interaction mechanism(s). The important criteria to consider for HPLC method development are resolution, sensitivity, precision, accuracy, limit of detection, linearity, reproducibility, time of analysis and robustness of the method. The quality of the column itself, and its performance over time, contribute in important ways to each of these criteria.

In spite of recent advances in the development of alternative stationary phases such as zirconia, alumina, titania, and polymer-based packings (K. K. Unger, *Packings and Stationary Phases in Chromatographic Techniques*, Marcel Dekker, New York, 1990), microparticulate silica is by far the most commonly employed chromatographic support in HPLC. This is mainly due to its versatility, high derivatization potential, high column efficiency, and easily controlled particle size and porosity. Most of the silica-based packings in use today are bonded phases that are formed by covalently attaching organic molecules with specific properties to silanol groups (Si—OH) present on the silica surface. Of these silica gel-based support materials, reversed-phase (i.e., weakly polar or non-polar) bonded packings are generally preferred because of their high resolution power, separation efficiency, and mechanical stability.

Although superior to most other available packings, silica-based bonded phases remain imperfect supports for reversed-phase HPLC, especially in the analysis of basic substances. The derivatization process that produces the bonded phase is rarely fully complete and generally leaves unreacted a significant number of silanol groups on the silica surface. The presence of these residual weakly acidic silanols leads to irreversible adsorption of basic solutes, high peak tailing, and a strong dependence of retention times on solute concentrations (H. Engelhardt et al., J. Chromatogr. 1988, 458: 79–92). Separations at high pH (i.e., pH 9 or greater) appear, therefore, attractive for certain basic analytes since, under these conditions, (1) such analytes would be in their free-base form, and (2) the unreacted weakly acidic silanol groups would be totally ionized, a situation where irreversible and potentially deleterious electrostatic interactions between solute molecules and stationary phase would be minimized. Furthermore, operating at a pH well above the $pK_a$ value of basic compounds should also allow more reproducible separations, since retention times changes due to the formation of ionized forms would not take place (J. J. Kirkland et al., J. Chromatogr. 1997, 762: 97–112; J. J. Kirkland et al., J. Chromatogr. A, 1998, 797: 111–120). However, using reversed-phase HPLC columns under intermediate to high pH aqueous conditions, especially at elevated temperatures, is known to result in rapid loss of column performance and in reduced column lifetimes due to deterioration of the packing material, largely through solubilization of the silica support (J. J. Kirkland et al., J. Chromatogr. A, 1995, 691: 3–19; C. S. Horvath et al., Anal. Chem. 1977, 49: 142–154; A. Wehrli et al., J. Chromatogr. 1978, 149: 199–210).

Several studies have been carried out to devise ways to extend the lifetime of reversed-phase HPLC columns. Thus, the use of untreated silica pre-columns that partially saturate the mobile phase with dissolved silica, thereby reducing or precluding solubilization of the packing material in the analytical column, has been found to significantly improve the longevity of a column (J. G. Atwood et al., J. Chromatogr. 1979, 171: 109–115). Addition to the mobile phase of a large variety of certain additives and modifiers, such as organics, salts and detergents (L. C. Sander and S. A. Wise, CRC Crit. Rev. Anal. Chem. 1987, 18: 299), that interact with the analytes and/or the stationary phase, has been reported to increase the lifetime of HPLC columns by, for example, preventing irreversible adsorption of basic solutes to the reversed-phase support and/or by decreasing the solubility of microparticulate silica at intermediate to high pH.

Chemical approaches have also been developed to extend the lifetime of reversed-phase HPLC columns by shielding, eliminating, or reducing the number of residual silanol groups on the silica surface (K. K. Unger, *Porous Silica*, Elsevier, Amsterdam, N.Y., 1976; J. Kohler and J. J. Kirkland, J. Chromatogr. 1987, 385: 125–150; D. B. Marshall et al., J. Chromatogr. 1986, 361: 71–82; J. G. Dorsey and W. T. Cooper, Anal Chem. 1994, 66: 857A–867A). Work has, for example, been directed at increasing the efficiency of the derivatization reaction in order to produce more densely bonded silica supports with a smaller number of unreacted silanols. Silanol groups have also been partially removed by curing, a condensation reaction of adjacent silanols (T. G. Waddell et al., J. Am. Chem. Soc. 1981, 103: 5303–5307), or by end-capping, a chemical process in which relatively small reagents (such as activated silanes) are reacted with the remaining silanols (G. B. Cox, J. Chromatogr. A, 1993, 656: 353–367; J. J. Kirkland et al., J. Chromatogr. A, 1997, 762: 97–112). Bonding of bidendate silanes or bulky silanes (J. J. Kirkland et al., Anal. Chem. 1989, 61: 2–11) with tentacle-like chains (M. Ashri-Khorassani, et al., Anal. Chem. 1988, 60: 1529–1533) has been shown to produce stationary phases with improved stability properties as compared with the commonly used monofunctional packings. Similarly, polymeric (T. Darling et al., J. Chromatogr. 1977, 131: 383–390; A. J. Alpert and F. E. Regnier, J. Chromatogr. 1979, 185: 375–392) and horizontally polymerized silanes (G. Schomburg et al., J. Chromatogr. 1983, 282: 27–39; M. J. Wirth and H. O. Fatunmbi, Anal. Chem. 1993, 65: 822–826) have been found to exhibit some stability in high pH mobile phases. In a slightly different approach, treatment of silica particles with metal oxides or hydroxides, which results in the formation of a protective layer over the silica, has also been demonstrated to increase the lifetime of the stationary phase thus obtained (see, for example, U.S. Pat. No. 4,600,646).

Although most of the modifications of the silica surface generate chromatographic supports with improved stability properties at medium to high pH, several of the chemical reactions cannot easily be applied to many of the currently commercially available columns.

Therefore, a need continues to exist for improved strategies for extending the lifetime of silica gel-based reversed-phase HPLC columns. There is a particular need for approaches that are widely applicable, do not involve chemical modifications of the stationary phase, increase the retention of analytes in the column, and yet preserve the integrity of the HPLC column.

Such strategies would for example be useful in the case of a particular superficially porous silica-based packing material that has been reported to show great performance for the separation of large molecules. This packing material, which is composed of particles made of a solid silica core and a macroporous shell, cannot practically be used at medium pH (i.e., 6–8) and at high temperature (i.e., >50° C.) since these conditions cause a dramatic shortening of its lifetime. Methods to increase the longevity of this packing material under the above conditions, which are typical for the analysis of some large biomolecules such as DNA, oligonucleotides, and some proteins, would considerably widen the range of applications of this chromatographic support. Furthermore, in the case of DNA fragments, it may be desired that the retention of the fragments take place in the order of the fragments' length regardless of their composition. A reverse order is sometimes observed due to interactions with silanol residues on the silica surface. Methods that would reduce or eliminate this problem and thus allow DNA fragment sizing are therefore highly desirable.

SUMMARY OF THE INVENTION

The present invention provides systems for performing reversed-phase high-performance liquid chromatography analyses. In particular, the present invention encompasses reagents and strategies for efficiently separating components of a sample mixture by reversed-phase HPLC while avoiding problems linked to column instability such as those generally observed under intermediate to high pH aqueous conditions. More specifically, the present invention provides additives for aqueous mobile phases, and silica gel-based reversed-phase HPLC methods that lead to high retention of the analytes in the column and to extended column lifetimes.

In one aspect, the present invention provides methods for analyzing, separating, isolating, and/or purifying components of a sample mixture by silica-based reversed-phase HPLC comprising the step of eluting the HPLC column, which is packed with a superficially porous silica-based reversed-phase support and loaded with the sample, mixture using an aqueous mobile phase comprising less than 10% by volume of at least one additive. In these methods, the presence of the additive in the mobile phase leads to an increased column lifetime as compared with the lifetime observed in the absence of the additive, all other conditions being equal. Additionally or alternatively, the presence of the additive in the mobile phase leads to a higher retention in the column of at least one component of the mixture as compared with the retention observed for the same component in the absence of the additive, all other conditions being equal.

In certain preferred embodiments, the additive is a neutral, polar fluorinated organic modifier. Preferably, the fluorinated organic modifier is a polyfluorinated alcohol. Polyfluorinated alcohols for use in the present invention include, but are not limited to, 2,2-difluoroethanol; 2,2,2-trifluoroethanol; 3,3,3-trifluoropropanol; 1H,1H-dihydropenta-fluoropropanol; 1,1,1,3,3,3-hexafluoroisopropanol; perfluoropropanol; 2-methyl-1,1,1,3,3,3-hexafluoro-2-propanol; 4,4,4-trifluoro-1-butanol; 3,3,4,4,4-penta-fluoro-2-butanol; 1H,1H-dihydroheptafluoro-1-butanol; 2,2,3,3,4,4,4-heptafluoro-1-butanol; and perfluoro-1-butanol. Preferred polyfluorinated alcohols for use in the inventive HPLC methods include 2,2,2-trifluoroethanol; 1,1,1,3,3,3-hexa-fluoroisopropanol; and combinations thereof.

In some embodiments, the pH of the aqueous mobile phase is between 2 and 11. Preferably, the pH of the aqueous mobile phase is between 6 and 8. In addition to the fluorinated additive, the mobile phase may further comprise one, or more than one, modifier selected from the group consisting of a buffering agent, an ion-pairing agent, a multivalent cation binding agent, a surfactant, and a water-soluble organic solvent. The mobile phase may be run through the HPLC column using an isocratic elution or a gradient elution.

Preferably, the silica-based bonded phase is selected from the group consisting of C4 (butyl), C8 (octyl), C18 (octadecyl), CN (cyano), and phenyl.

The inventive methods may be used to analyze, detect, separate, isolate, and/or purify any compound, agent, or molecule that can be loaded on and eluted through a silica gel-based reversed-phase HPLC column. In certain embodiments, at least one of the components of the mixture is detected as it elutes from the column as a solution in the mobile phase. In other embodiments, the HPLC method allows the analysis of at least one component of the mixture. In still other embodiments, at least one of the components of the mixture is collected in a distinct fraction as it emerges from the column as a solution in the mobile phase. In yet other embodiments, the HPLC method allows the preparative isolation of at least one component of the mixture.

The inventive methods may, in particular, be used to analyze, detect, separate, isolate, and/or purify small organic molecules, natural products, as well as biomolecules such as polypeptides, polynucleotides, and oligonucleotides.

In certain preferred embodiments, the inventive HPLC methods are used for analyzing, detecting, separating, isolating, and/or purifying DNA fragments. The additive in the aqueous mobile phase is preferably a polyfluorinated alcohol selected from the group consisting of 2,2,2-trifluoroethanol; 1,1,1,3,3,3-hexafluoroisopropanol; and combinations thereof. The mobile phase may further comprise at least one ion-pairing agent, at least one multivalent cation binding agent, and at least one water-soluble organic solvent. In preferred embodiments, the ion-pairing agent is a trisubstituted ammonium salt; the multivalent cation binding agent is ethylenediaminetetraacetic acid (EDTA); and the water-soluble organic solvent is acetonitrile. The mobile phase may be run through the HPLC column using an isocratic elution or a gradient elution. Preferably, a gradient is used.

Other aspects, features and advantages of the present invention will become apparent from the following detailed description. It should be understood, however, that the detailed description and specific examples, while indicating preferred embodiments of the invention, are given by way of illustration only.

DEFINITIONS

Figure 1A:
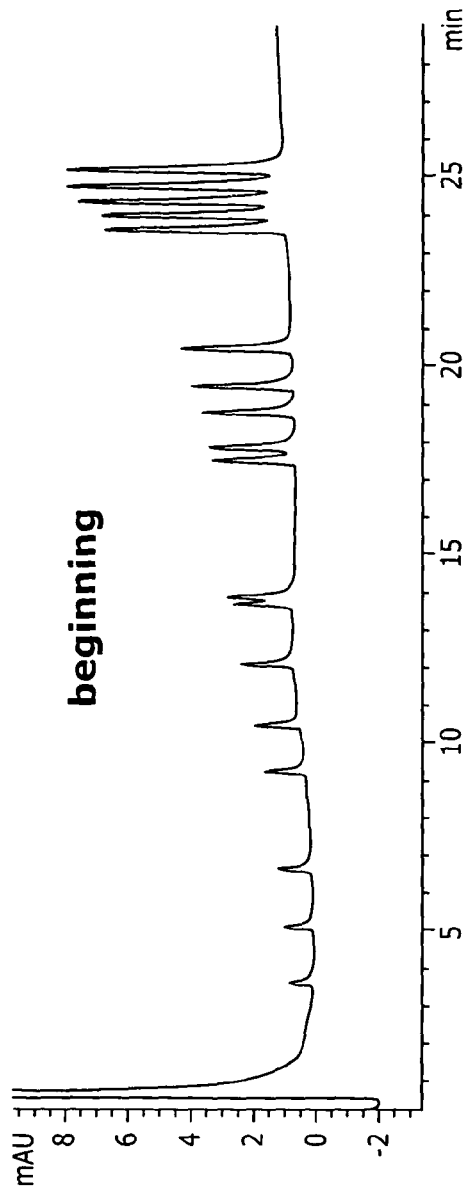
FIG. 1 illustrates the effects of column aging on the separation of DNA fragments. Part A of FIG. 1 shows a chromatogram obtained by injecting a pbr 322 Hae III DNA digest sample (2 μL) on a Poroshell C18 HPLC column. The conditions of the chromatographic run were as follows: Mobile phase, solvent A: 0.1 M TEAA/0.1 mM EDTA, pH=7, solvent B: A in 25% acetonitrile; Gradient: 40–80% B in 30 minutes; Flow rate: 0.25 mL/mn; Column temperature: 50° C. Part B of FIG. 1 shows a chromatogram obtained under the same experimental conditions 62 hours after that displayed in part A. Between the two injections of DNA digest, the column was "aged" in a controlled manner as described in Example 1.

Throughout the specification, several terms are employed, that are defined in the following paragraphs.

The term "HPLC" has herein its art understood meaning and refers to a particular type of liquid chromatography that characteristically operates under high-pressure conditions. In a liquid chromatography system, the molecules of "analytes" (i.e., compounds or agents under investigation) interact with two non-miscible phases: a "stationary phase" (the solid support contained within a column chromatography), and a "mobile phase" (the liquid media that is run through the column and acts as a carrier for the analytes). Preferred stationary supports for use in the present invention are silica gel-based reversed-phase packings. In the context of the present invention, analytes may be any chemical or biological molecule, compound, agent, or moiety that can be analyzed by silica-based reversed-phase HPLC. Analytes (also called solutes) include, but are not limited to, small organic molecules, natural products, and biomolecules such as polypeptides, polynucleotides and oligonucleotides. Particularly preferred analytes are DNA molecules.

The term "reversed-phase", as used herein to characterize a mode of chromatography, refers to a method or a process in which the mobile phase is more polar than the stationary phase. In reversed-phase chromatography, hydrophobic compounds that exhibit more affinity for the hydrophobic, less polar stationary phase than for the mostly aqueous mobile phase, elute less quickly than do hydrophilic compounds. Reversed-phase chromatography is generally used for the study of non-polar or weakly polar water-soluble molecules; however, more polar molecules can also be separated by using a more polar bonded phase or other techniques such as ion-pair chromatography. In contrast, the term "normal phase", refers to a method or a process in which the mobile phase is less polar than the stationary phase. In normal phase chromatography, hydrophobic analytes that exhibit more affinity for the mobile phase than for the stationary phase, elute more quickly than do hydrophilic compounds. Normal phase chromatography is generally used for the study of organic molecules that are not soluble in water or aqueous solutions.

The term "superficially porous stationary support", as used herein, refers to a solid support composed of a packing material having surface pores. More specifically, the particles of solid support have a solid core and a thin porous shell.

The term "aqueous mobile phase", as used herein, refers to a liquid that is mainly aqueous (i.e., non-organic) in character. In the context of the present invention, an aqueous mobile phase may comprise a certain amount of organic solvent, as well as other additives and modifiers. The amount of organic solvent may vary (for example, from 0 to 100%) during the chromatographic run. The term "organic solvent", as used herein, refers to any organic (i.e., non-aqueous) liquid that is suitable for use in reversed-phase chromatographic separations. Preferably, the organic solvents for use in the present invention are polar (e.g., more polar than the reversed-phase stationary support material) and water soluble.

The mobile phase may be eluted through the chromatography column using an isocratic elution or a gradient. The terms "gradient" and "gradient elution" are used herein interchangeably. They refer to an elution process that involves changes in the mobile phase composition during the chromatographic run. The mobile phase composition may be changed continuously or stepwise during the elution process. The composition may be varied to modify the character or properties (e.g., elution strength, polarity or pH) of the mobile phase. A gradient elution is generally used to decrease the time necessary to separate components of a mixture. In an "isocratic elution", the composition of the mobile phase remains essentially constant for any part or all of the duration of the chromatographic separation process, however, the concentrations of the mobile phase components may vary. Thus, the term "isocratic" refers to an elution process in which the concentrations of the components of the mobile phase are maintained constant (i.e., within ±0.1%, preferably within ±0.05%) throughout the separation.

In a HPLC system, a detector is generally placed downstream from the analytical column, and is used to continuously monitor whole or part of the eluant exiting the column. A "detector" typically responds to a property of the analyte (e.g., absorbance, fluorescence, chemiluminescence, optical activity, radiochemical or electrochemical property, mass) or to a property of the mobile phase (e.g., index of refraction, thermal conductivity).

The term "chtromatogram" has herein its art understood meaning. It refers to a plot corresponding to the detector response as a function of time. Ideally (i.e., in the absence of co-elution) each peak in a chromatogram corresponds to a single analyte. The elution time of the analyte (or retention time of the peak) provides evidence for the identity of the analyte (qualitative analysis) and the height or area of the peak can be related to the concentration of the analyte (quantitative analysis).

The term "retention time" refers to a measure of the elution time of an analyte (i.e., the time needed, after injection, for an individual solute to reach the detector). The retention time reflects the extent of retention (or retardation) undergone by a particular analyte in a specific HPLC column under given mobile phase and elution conditions (the higher the retention time, the stronger the interactions between the chromatographic support and the solute). When comparing the retention times of a given compound or molecule using different chromatographic systems (e.g., different stationary phases and/or different mobile phases), it is necessary to correct the retention time values for the time it takes the mobile phase alone to reach the detector.

The terms, "durability", "longevity" and "lifetime" are used herein interchangeably. They refer to a time period during which a HPLC column can be used without undergoing significant loss of performance. These terms also refer to the number of analytical injections that can be performed before observing significant loss in column performance. Column performance is a function of selectivity, specificity, stability and reproducibility.

As used herein, the term "selectivity" refers to a parameter that measures the relative retention of two particular compounds on a given chromatography column (the higher the selectivity, the better the separation). When operating under constant experimental conditions, shifts in selectivity are an indication of problems with loss of bonded phase or column fouling.

The term "specificity" refers to the ability of a chromatographic method to measure accurately and specifically an analyte of interest in the presence of other components that may be expected to be present in the sample. It is a measure of the degree of interference from other ingredients, excipients, impurities, and degradation products, ensuring that a peak response is due to a single component only (i.e., that co-elution does not take place). In a separation, specificity is measured and documented by the resolution, efficiency (i.e., plate count), and peak tailing.

As used herein, the term "resolution" refers to the difference in retention of adjacent peaks divided by their average band width. Sufficient resolution between peaks is required for proper quantitation and efficient separation of different analytes.

The terms "column efficiency" or "theoretical plates" are used herein interchangeably. They have their art understood meaning and refer to a measure of the efficiency, or resolving power, of a chromatography column. The efficiency of a column can be measured by several methods. A description and an evaluation of such methods have been reported by B. A. Bidlingmeyer and F. V. Jr. Warren (in: Anal. Chem. 1984, 56: 1583–1596). The most common reasons for loss of column efficiency (or theoretical plates) are column voiding and column fouling. Decreasing efficiency leads to broadening of the peaks in the chromatogram.

The term "tailing", as used herein, refers to a peak that does not exhibit a Gaussian (symmetric) shape, but in which the front part is steeper than the rear. Tailing may be caused by column voiding or by the presence of sites on the packing material exhibiting a stronger than average retention for the solute.

The term "stability", as used herein, refers to the ability of a chromatography column to retain its specificity, selectivity, and reproducibility properties over a long period of time.

The term "reproducibility", as used herein, is a measure of the degree of repeatability of a HPLC method under normal operation. It is usually expressed as the percent relative standard deviation for a statistically significant number of samples.

The term "column voiding", has herein its art understood meaning, and refers to the formation of an empty space, most often at the head of a HPLC column. Column voiding may be observed in poorly packed columns, or may be caused by solubilization of silica or by excessive system back pressure due to poorly operating pumps or sample injection valves. Column voiding leads to efficiency drop, decreased resolution, peak broadening and peak tailing. "Column fouling" results from a buildup of retained material on the stationary phase, which partially or totally prevents elution. Column fouling can lead to shifts in peak retention and to loss of resolution.

Other parameters, such as the capacity factor and column back pressure, may help evaluate the operating conditions of a HPLC column. The term "capacity factor" has herein its art understood meaning and refers to a measure of retention independent of flow rate and column dimensions. Changes in the capacity factor under constant chromatographic conditions may indicate either problems with loss of bonded phase or problems with column fouling due to non-eluting compounds. When the "column back pressure" increases, it is almost always due to particulates that have collected on the column inlet frit. However, column voiding induced by column packing collapse can cause a large surge in pressure.

In the context of the present invention, the term "additive" refers to any molecule, compound, agent, or moiety that can be added to an aqueous mobile phase and whose presence in the mobile phase leads to a higher retention in the HPLC column of at least one of the components of the sample mixture under investigation, as compared with the retention that is observed for the same component of the mixture in the absence of the additive, all other conditions being equal. Alternatively or additionally, the presence of such an additive in the mobile phase may lead to an increased column lifetime, as compared with the lifetime observed in the absence of the additive, all other conditions being equal. Preferred additives for use in the present invention are fluorinated neutral organic modifiers.

The terms "peptide", "polypeptide", and "protein" are used herein interchangeably. They refer to sequences of more than three amino acids. The peptides may be in their neutral (uncharged) forms or as salts, and either unmodified or modified by glycosylation, side chain oxidation, or phosphorylation.

The term "polynucleotide", as used herein, refers to a nucleic acid molecule (i.e., an RNA (ribonucleic acid) or DNA (deoxyribonucleic acid) polynucleotide, including portion of a genomic polynucleotide, cDNA, and synthetic polynucleotide). Preferably, a polynucleotide is at least 5 nucleotides long. The definition encompasses single stranded and double stranded polynucleotides.

As used herein, the term "ion-pair chromatography" refers to a chromatographic method for separating sample mixtures in which some or all of the sample components contain functional groups that are ionized or can undergo ionization. Ion-pair chromatography is typically carried out with a reversed-phase column in the presence of an ion-pairing agent. The term "ion-pairing agent", as used herein, refers to a reagent, which is added to the mobile phase and interacts with ionized or ionizable groups in sample compounds to improve resolution in a chromatographic separation. Anionic and cationic ion-pairing agents are known in the art.

Additional definitions are provided throughout the Detailed Description.

DETAILED DESCRIPTION OF CERTAIN PREFERRED EMBODIMENTS

The present invention relates to improved HPLC systems. In particular, the present invention provides additives for aqueous mobile phases and silica gel-based reversed-phase HPLC methods that lead to high retention of analytes in the column, to good resolution and separation of components of sample mixtures, as well as to extended HPLC column lifetimes.

I. Silica-Based Reversed-Phase HPLC Methods

One aspect of the present invention relates to new HPLC methods. More specifically, the present invention provides methods for analyzing, detecting, separating, isolating, and/or purifying components of a sample mixture by silica-based reversed-phase HPLC. The inventive methods comprise a step of eluting the HPLC column, which is packed wit a superficially porous silica-based reversed-phase support and loaded with the sample mixture, using an aqueous mobile phase comprising less than 10% by volume of at least one additive. In preferred embodiments, the additive is a fluorinated neutral polar organic modifier.

Mobile Phase Additives

According to the instant invention, the presence of the additive in the aqueous mobile phase leads to a higher retention in the HPLC column of at least one component of the sample mixture under investigation as compared with the retention that is observed for the same component of the mixture in the absence of the additive, all other conditions being equal. Preferably, the presence of the additive in the mobile phase leads to a higher retention in the column of more than one component of the sample mixture; more preferably, the presence of the additive in the mobile phase leads to a higher retention of most of the components of the mixture (e.g., more than 50%, 60%, 75% of the components or more; preferably more than 60% or 70% of the components); most preferably, the presence of the additive in the mobile phase leads to a higher retention of all the components of the mixture. A higher retention of the analytes in the HPLC column generally results in a greater resolution and better separation of the components of the sample mixture.

A higher retention of a particular solute in the HPLC column may be defined as a significant increase in the retention time of that particular solute (the increase in retention time will highly depend on the analyte). A higher retention of a particular solute in the HPLC column may also be defined as an increase in retention time that is sufficient to resolve two components of interest of the sample mixture. A higher retention of a particular analyte in the HPLC column may also correspond to an increase in retention time that is sufficient to allow separation, isolation and/or purification of that particular analyte by, for example, preventing co-elution of other components, excipients, impurities, and/or degradation products.

In certain preferred embodiments, the presence of the additive in the aqueous mobile phase alternatively or additionally leads to an increased lifetime of the HPLC column as compared with the lifetime that is observed in the absence of the additive, all other conditions being equal. In the context of the present invention, an increased lifetime of the HPLC column corresponds to an increase of the time period during which the column substantially retains its selectivity, specificity, and reproducibility properties. An increased lifetime of the HPLC column may also be defined as an increase in the number of analytical injections that can be performed before significant loss in column performance occurs. Preferably, the presence of the additive in the aqueous mobile phase leads to at least a 200% increase in the number of injections; more preferably, to at least a 300% increase in the number of injections; most preferably, to at least a 500% increase in the number of injections. Loss of performance of HPLC columns may be monitored by different methods; lower retention times, peak broadening, peak tailing, high back column pressure, and loss of theoretical plates, are all indicative of column deterioration and loss of performance.

Additives for use in the present invention may be any water-soluble entity that can be added to an aqueous mobile phase to achieve the desired effect(s). Other properties of the additive that may be desirable include, but are not limited to, low viscosity, ultraviolet (UV) transparency (to allow easy detection of eluted analytes by absorption); high volatility (for ease of removal after isolation of the fraction of interest); and low toxicity (in particular, when the HPLC analysis is carried out on compounds or agents that are subsequently used in biological systems, e.g., cell culture, or utilized as pharmaceuticals or diagnostic probes, e.g., in mammals, including humans).

Preferred additives are neutral, polar fluorinated organic modifiers. Fluorinated organic modifiers for use in the inventive HPLC methods may be any organic molecule, compound, agent, or moiety that (1) can be added homogeneously to an aqueous mobile phase in a quantity corresponding to less than 10% of the mobile phase total volume; (2) contains at least one fluorine atom; (3) is neutral, and (4) is polar.

Preferably, neutral, polar fluorinated organic modifiers are polyfluorinated alcohols. The preferred polyfluorinated alcohols for use in the practice of the present invention are molecules comprising from 2 to 10 carbon atoms, and bearing at least one hydroxyl group (OH) and more than one fluorine atom. Preferably, a polyfluorinated alcohol comprises between 2 and 5 carbon atoms, and bears one hydroxyl group and at least two fluorine atoms. Thus, a polyfluorinated alcohol may be, for example, an ethanol, n-propanol, isopropanol, n-butanol, isobutanol, tert-butanol, or n-pentanol derivative. Suitable polyfluorinated alcohols for use in the inventive HPLC methods include, but are not limited to, 2,2-difluoroethanol ($CHF_2CH_2OH$); 2,2,2-trifluoroethanol ($CF_3CH_2OH$); perfluoroethanol ($CF_3CF_2OH$); 3,3,3-trifluoro-1-propanol ($CF_3CH_2CH_2OH$); 1H,1H-dihydropentafluoro-propanol ($CF_3CF_2CH_2OH$); 1,1,1,3,3,3-hexafluoroisopropanol ($CF_3CH(OH)CF_3$); perfluoropropanol ($CF_3(CF_2)_2OH$); 4,4,4-trifluoro-1-butanol ($CF_3(CH_2)_3OH$); 2-methyl-1,1,1,3,3,3-hexafluoro-2-propanol ($CF_3C(CH_3)OHCF_3$); 3,3,4,4,4-pentafluoro-2-butanol ($CF_3CF_2CH(OH)CH_3$); 2,2,3,3,4,4,4-heptafluoro-1-butanol ($CF_3(CF_2)_2CH_2OH$); and perfluoro-1-butanol ($CF_3(CF_2)_3OH$). The preferred polyfluorinated alcohols are 2,2,2-trifluoroethanol; 1,1,1,3,3,3-hexafluoroisopropanol; and combinations thereof.

Polyfluorinated alcohols are commercially available from, for example, Sigma-Aldrich (Milwaukee, Wis.), Alfa Aesar (Ward Hill, Mass.), Acros Organics (Pittsburgh, Pa.); Halocarbon Products Corporation (River Edge, N.J.), and Narchem Corporation (Chicago, Ill.). Polyfluorinated alcohols may also be synthesized, for example, using the preparative methods previously reported by J. Chen et al. in Inorg. Chem. 1996, 35: 6676–6681.

The aqueous mobile phase may comprise one or more than one additive. The additive (or combination of additives) is added to the mobile phase in a quantity that corresponds to less than 10% of the mobile phase total volume and that is sufficient to achieve the desired effect(s). Preferably, the mobile phase comprises less than 5% by volume of the additive. More preferably, the mobile phase comprises between 0.5% and 2% by volume of the additive. The concentration of additive(s) in the mobile phase may be optimized based on the nature of the additive(s), the chromatographic support material selected for the analysis, the compounds to be analyzed and/or separated, and the desired degree of separation.

Mobile Phase

In carrying out analyses, separations, isolations and/or purifications according to the inventive reversed-phase HPLC methods, the aqueous mobile phase comprises less than 10% by volume of at least one additive, as described above. In addition to water and the additive(s), the mobile phase may also contain other components. The selection of the aqueous mobile phase components (i.e., various modifiers and other additives) will vary depending on the nature of the separation to be performed. Any of a number of mobile phase components typically employed in reversed-phase HPLC are suitable for use in the methods of the present invention.

Pre-requisites for mobile phase additives and modifiers include high purity (e.g., commercially available HPLC grade) and absence of reactivity toward the packing material as well as toward the analytes. The resulting mobile phase (i.e., the mobile phase comprising the different additives and modifiers) must ensure the solubility of all the components of the sample mixture to be analyzed.

The nature and concentration of the mobile phase components will vary depending on the separation to be carried out. In addition to varying from sample to sample, the mobile phase composition and/or the concentration of the mobile phase components may be varied over the course of the elution process. Thus, according to this aspect of the invention, the mobile phase may be run through the HPLC column using an isocratic elution or a gradient elution in order to both enhance resolution and decrease elution time.

In certain preferred embodiments, in addition to water and the fluorinated additive, the aqueous mobile phase may further comprise one, or more than one, modifier selected from the group consisting of a buffering agent, an ion-pairing agent, a multivalent cation binding agent, a surfactant, and an organic solvent.

Organic solvents that may be added to the aqueous mobile phase include any non-ionic, organic (i.e., non-aqueous), water-soluble liquid suitable for use in silica gel-based reversed-phase HPLC columns. Other desirable properties of a water-soluble organic solvent include, but are not limited to, high purity, low boiling point, low viscosity, low cost (in particular in preparative separations) and good ultraviolet cut-off. Preferred water-soluble organic solvents for use in the inventive HPLC methods are polar solvents. Exemplary suitable polar solvents are alcohols, ketones, nitriles, amides, esters, and alkylsulfoxides. More specifically, suitable polar solvents for use in the inventive HPLC methods include, for example, acetonitrile, methanol, ethanol, n-propanol, isopropanol, dimethylformamide, methyl acetate, ethyl acetate, acetone, methyl ethyl ketone, dimethylsulfoxide, and tetrahydrofuran.

The presence of an organic solvent in the aqueous mobile phase may result in a variation in the eluting strength of the mobile phase. Acetonitrile and methanol are among the most commonly used reversed-phase solvents because of their low viscosity, favorable vapor pressure, ultraviolet transparency, and particularly because of their elution strength.

Addition of organic solvent to the aqueous mobile phase may also help in the dissolution of weakly water-soluble analytes. Furthermore, organic solvents such as acetonitrile and isopropanol, that are often used in reversed-phase elution, are known to have chaotropic (complex breaking) effects on hydrophobic aggregates. This property is particularly useful in the case of oligonucleotides that have a tendency to form hydrophobic, hydrogen-bonded complexes, which complicates their separation and purification.

In certain preferred chromatographic methods of the invention, the water-soluble organic solvent is present in the aqueous mobile phase in an amount that is sufficient to selectively reduce the retention of the analytes that otherwise undergo strong interactions with the stationary support material (the higher the concentration of organic solvent in the mobile phase, the shorter the retention time of the solutes). A single organic solvent or a combination of organic solvents may be added to the aqueous mobile phase to obtain the desired effect(s). Preferably, the aqueous mobile phase comprises a single organic solvent or a mixture of two different organic solvents.

The concentration and type of organic solvent(s) may be varied to a significant extent to alter the interactions and modulate the retention times in order to optimize the separation. The volume of water-soluble organic solvent (or of the combination of organic solvents) in the mobile phase may suitably be varied from 0 to 100 percent, with the higher concentrations being employed for the more strongly retained solutes. Samples are typically eluted by starting with an aqueous or mostly aqueous mobile phase and progressing to a mobile phase containing increasing amounts of organic solvent. Any of a number of combinations of organic solvents and gradient or isocratic elution profiles may be used in the practice of the HPLC methods of the invention.

As already mentioned above, the pH of the mobile phase influences the retention of ionized or ionizable analytes in a reversed-phase HPLC column by affecting the nature, strength and/or mechanism of the interactions taking place between the solute molecules and the chromatographic packing material. Controlling the pH of the mobile phase provides a means to increase analytes retention times and to extend column lifetimes (for example, by favoring non-specific (i.e., weak) interactions over electrostatic (i.e., strong) ones and/or by preventing irreversible and potentially deleterious interactions to occur).

The pH of the aqueous mobile phase in the inventive HPLC methods may be varied by addition of buffering agents. The choice of the buffering agent is typically governed by the desired pH (which itself depends on the nature of the analytes and of the chromatographic support material selected). The choice of the buffering agent may also be influenced by the nature of the organic solvent present in the mobile phase (as buffers and organic solvents are not always soluble). Suitable buffers for use in the present invention include, but are not limited to, phosphate, citrate, carbonate, acetate, and Tris buffers. The buffering capacity is generally enhanced at high concentrations of buffer; higher buffer concentrations usually give more symmetrical peak shapes of molecules that are partially ionized at the pH of the mobile phase, by reducing local perturbations of the migrating analytes. Suitable buffer concentrations for use in the inventive HPLC methods are lower than 100 mM. Preferably, the buffer concentration is between 10 and 50 mM.

Ion-pairing agents constitute another type of modifiers that can be added to the mobile phase. An ion-pairing agent is an entity that interacts with ionized or ionizable functional groups on an analyte to improve the resolution of a chromatographic separation. Ion-pair high-performance liquid chromatography has long been a method of choice for the analysis, isolation, separation, and/or purification of highly polar and ionic molecules, including many pharmacologically and clinically important drugs (G. Inchauspe et al., J. Chromatogr. 1987, 404: 53–66), and biomolecules such as polypeptides and polynucleotides (C. Olieman and D. Voskamp, in "CRC Handbook of HPLC for the Separation of Amino Acids, Peptides, and Proteins" W. S. Hancock (Ed.), Vol. 1, CRC Press, Boca Ration, Fla., 1984, pp. 161–165), including double-stranded DNA and DNA fragments (U.S. Pat. Nos. 5,585,236 and 5,795,976; C. G. Huber et al., Anal. Biochem. 1993, 212: 351–358). Various modifications and improvements of the ion-pairing chromatography method have been patented (see, for example, U.S. Pat. Nos. 6,024,878; 6,056,877; and 6,287,822).

Any of a number of ion-pairing agents may be used in the inventive HPLC methods, including cationic and anionic ion-pairing agents.

Suitable anionic ion-pairing agents include perfluoroalkanoic acids (e.g., trifluoroacetic acid (TFA) and higher homologues). Trifluoroacetic acid ($CF_3COOH$) is often preferred because of its high volatility, which allows easy removal from preparative fractions, and because of its favorable absorbance properties (the UV absorbance spectrum of TFA peaks at 200 nm), which create minimal interference with detection of analytes at low wavelengths. TFA is most often present in a mobile phase at a concentration of 0.1%, although lower concentrations ranging from 0.05 to 0.08% have successfully been used.

Suitable cationic ion-pairing agents for use in the present invention include lower primary, secondary and tertiary amines, such as triethylamine, and lower trialkylammonium salts of organic or inorganic acids, or lower quaternary ammonium salts. For example, the ion-pairing agent may be triethylammonium acetate, tetramethyl ammonium acetate, diethylammonium acetate, propylethylammonium acetate, butylammonium acetate, dimethyldiethylammonium acetate, methylhexylammonium acetate, propyldiethylammonium acetate, tetraethylammonium acetate, octylammonium acetate, tripropylammonium acetate, octadimethylammonium acetate, decylammonium acetate, tetrapropylammonium acetate, tributylammonium acetate, tetrabutylammonium acetate, octadecylammonium acetate, pyridinium ammonium acetate, cyclohexylammonium acetate, and combinations thereof. A preferred ion-pairing agent is often triethylammonium acetate (TEAA). Instead of acetate, the anionic counterpart of the cationic ion-pairing agent may be a carbonate, bicarbonate, phosphate, sulfate, nitrate, propionate, formate, chloride, perchlorate, or bromide.

The nature, concentration, and hydrophobicity of an ion-pairing agent of choice will depend on the number and types (i.e., cationic or anionic) of charged sites on the components of the sample mixture to be separated. The concentration of the ion-pairing agent in the mobile phase is typically between about 50 mM and 1.0 M; preferably between 50 mM and 200 mM. Generally, increasing the concentration of the ion-pairing agent results in a better sample resolution.

Multivalent cation binding agents may also be added to the aqueous mobile phase. The importance of maintaining an environment free of multivalent cations in ion-pair chromatography systems, in particular for the analysis, separation and/or purification of nucleic acids, has been comprehensively described in U.S. Pat. No. 5,772,889.

Multivalent cation binding agents may be any molecule, compound, agent or chemical moiety that is water-soluble, has the ability to participate in the formation of a complex (containing more than one coordinate bond) with multivalent cations, and does not interfere with the chromatographic separation. It is also desirable that the complex formed between the multivalent cation binding agent and the metal contaminant be soluble in the mobile phase and that neither the multivalent cation binding agent nor the complex precipitate when an organic solvent is added to the mobile phase or when the volume of the organic solvent is increased over the course of the elution process. Suitable multivalent binding agents are chelating agents and crown ethers. Specific examples include, but are not limited to, acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α, α'-bipyridine, 4-hydroxybenzothiazole, 8-hydroxyquinaldine, 8-hydroxyquinoline, 1,10-phenanthroline, picolinic acid, quinaldic acid, α, α',α"-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. In the inventive HPLC methods, a preferred multivalent cation binding agent is EDTA.

A multivalent cation binding agent is usually present in the mobile phase at a concentration between 0.05 mM and 10 mM. Preferred concentrations of the multivalent cation binding agent are between 0.1 mM and 1 mM.

The mobile phase may also comprise a detergent (or surfactant). The presence of a surfactant in a reserved-phase HPLC mobile phase is often required to solubilize relatively insoluble analytes, such as membrane proteins (J. P. Andersen et al., Biochem. 1986, 25: 6439–6447) and in certain ion-pair HPLC methods, the presence of surfactants is necessary in order to achieve good separation conditions (*Ion-Pair Chromatography*, M. T. Hearn (Ed.), M. Dekker, New York 1985; *High Performance Liquid Chromatography in Biochemistry*, A. Henschen et al., (Eds.), Verlag Chemie, Weinheim, 1985).

Surfactants are generally water-soluble surface-active agents comprised of a hydrophobic portion, usually a long alkyl chain, attached to hydrophilic or water solubility enhancing functional groups. Surfactants can be categorized according to the charge present in the hydrophilic portion of the molecule (after dissociation in aqueous solution): anionic or cationic surfactants (such as sodium dodecyl sulfate (SDS)), ampholytic (i.e., zwitterionic) surfactants, and nonionic surfactants (such as Triton X-100, Brij, N-octylglucoside, and Tween 80).

However, detergents can also heavily interfere with reversed-phase chromatographic separations. When the concentration of detergent increases above a particular absolute mass on the HPLC column, peaks start to broaden (H. Kawasaki et al., Anal. Biochem. 1990, 191: 332–336), elute in poorly defined envelopes, or elute at or near the retention time of the detergent. In reversed-phase HPLC separations, detergent concentrations in the mobile phase are often kept below 0.1%.

When the HPLC is coupled to a Mass Spectrometer, the use of a nonionic detergent, such as β-D-glucopyranoside, which is compatible with the MS analysis, may be preferred (B. E. Chong et al., Rapid Commun. Mass Spec. 1999, 13: 1808–1812; C. L. Nilsson et al., Anal. Chem. 2000, 72: 2148–2153; B. E. Chong et al., Anal. Chem. 2001, 73: 1219–1227).

In addition to selecting parameters such as pH, elution profile, nature and concentration of the different additives and modifiers, the flow rate of the mobile phase may also be adjusted to achieve optimal separation. In HPLC, the upper flow rate depends on the pressure that results from pushing the mobile phase through the column and on the nature of the solid support and packing of the stationary phase. Typically, pressures in the range of from 200 to 12,000 psi may be used. Preferably, the pressures used are in the range from 600 to 3000 psi.

Stationary Phase

The inventive HPLC methods may be carried out using any suitable silica gel-based reversed-phase stationary support composed of superficially porous particles (i.e., microparticulate silica having a solid core and a thin porous shell). These particles allow for a rapid mass transfer in and out the thin porous shell. More specifically, the use of superficially porous particles (as opposed to completely porous particles) avoids the problem of macromolecules sticking inside the pores, and results in considerably improved resolution by, at least in part, enhancing the interaction of the solute molecules with the modified silica surface, which, in turn, increases the speed of separation and product recovery.

Any variety of silica-based reversed-phase chromatographic material may be used in the HPLC methods of the present invention. The stationary phase should be hydrophobic and less polar than the starting mobile phase. Particularly effective column packings are silica-based solid support that are alkylated. The term "alkylated", as used herein to characterize a solid support, refers to attachment of hydrocarbon chains to the silica surface. The hydrocarbon chain may be saturated or unsaturated and may optionally contain additional functional groups attached thereto. The hydrocarbon chains may be branched or straight chains, and may contain cyclic groups such as cyclopropyl, cyclopropylmethyl, cyclobutyl, cyclopentyl, cyclopentylethyl, and cyclohexyl.

Typically, the silica particle is derivatized to possess alkyl groups containing 3 or more than 3 carbon atoms, generally between 3 and 32 carbon atoms, and preferably between 4 and 18 carbon atoms. Such chemically bonded alkyl phases are commonly produced by the reaction of surface silica silanols with organochlorosilanes, and are commercially available.

Preferred silica-based bonded alkyl column packings for use in the present invention are butyl (C4), octyl (C8) and octadecyl (C18) modified silica particles. The interactions of these chromatographic beds with organic analytes are based on non-specific hydrophobic affinities. C18 is generally the most popular packing material for small molecules separation, while C8 is common for non-polar organics when C18 provides too much retention. In biological applications, C18 is particularly useful for the analysis of peptides, while C4 is often preferred for large proteins. Oligonucleotides are usually run on C18 columns although small oligonucleotide molecules separate well on C8.

Other suitable silica gel-based reversed-phase stationary supports include phenyl and cyano (CN) modified silica. Propylphenylsilane ligands attached to the silica particle show weak dipole-induced dipole interactions with polar analytes, and some specific interactions with amino compounds. A cyano modified surface is very slightly polar and often used for fast separations of mixtures consisting of very different components.

The selection of the type of stationary phase is governed by the nature of the solutes to be analyzed, separated, and/or purified. When the chromatographic support undergoes strong interactions with analyte molecules as compared with the interactions between the solutes and the mobile phase, very long retention times are observed, a situation, which is not analytically useful. A stationary phase must therefore be selected to provide weak to moderate solute interactions relative to the interactions taking place between the analytes and the mobile phase.

Column efficiency and peak resolution can be substantially increased by reducing the particle size. The term "particle size" refers to the average diameter of the spherical silica particle. Any of a large variety of silicas with different particle sizes may be used in the practice of the inventive HPLC methods. For analysis purposes, silica-based packing materials usually have particle sizes of 1 μm, 3 μm, 5 μm, or 10 μm (with smaller particles giving higher efficiencies for constant column length). Particles with average diameters >10 μm (i.e., in the 10–15 μm, 15–20 μm, or 20–30 μm range) are generally used for preparative separations. The size (i.e., length and diameter) of the silica-based reversed-phase HPLC column for use in the present invention will similarly depend on the goal of the chromatographic separation (i.e., analytical or preparative), as well as on the nature of the analytes.

The temperature of the HPLC column may also be controlled during the chromatographic run. An increase in temperature usually leads to a better resolution and separation of analytes. However, the operating temperature range for silica-based columns is 5 to 90° C. However, use of higher temperatures is known to shorten column lifetime. Signs of column damage include changes in retention times, loss of resolution, and high back column pressure.

II. Uses of the Silica-Based Reversed-Phase HPLC Methods

In certain preferred embodiments, the inventive HPLC methods described herein further comprise detecting at least one of the components of the mixture as it elutes from the column as a solution in the mobile phase.

Detection Methods

The detection may be carried out using any of a number of methods. In the HPLC setup, one (and sometimes more than one) detector is usually placed downstream from the analytical column and is used to continuously monitor the eluant (or, at least a small fraction of the eluant) as it exits the column. The detector may be chosen to respond to a property of the mobile phase, such as index of refraction and thermal conductivity. The presence of analytes in the column eluant is evidenced by a variation in the property monitored. The presence of analytes may also be recorded by detecting a change in UV-VIS absorption at a set wavelength, a change in fluorescence emission after excitation using a suitable wavelength, a change in optical activity, in light scattering, in the radiochemical response, or in the electrochemical response. Measurement of picogram to femtogram levels of clinical, pharmaceutical, environmental, and biological compounds can be made easily and reliably using selective and sensitive chromatographic detection systems.

One of the most important developments in liquid chromatography over the past several years has been its merger with mass spectrometry. Mass spectrometers have been interfaced with HPLC systems (LC/MS) to provide a means to identify the separated analytes as they elute from the column and to lower their limits of detection. Reversed-phase chromatography coupled to electrospray ionization (ESI) mass spectrometry or to matrix-assisted laser desorption ionization (MALDI) mass spectrometry has become a valuable tool for molecular weight determination as well as for providing other detailed and specific information about molecular structures. Reversed-phase LC/MS has, for example, been used to sequence picomole quantities of proteins and peptides, determine carbohydrate structures, detect post-translational modifications to proteins, and assess quality control of complex products.

Analytical and Preparative Separations

In certain embodiments, the inventive methods allow the analysis of at least one component of the sample mixture under investigation. In other embodiments, the inventive methods allow the preparative isolation of at least one component of the sample mixture.

In an analytical separation, the analytes may or may not be collected as they exit the HPLC column; preferably, the analytes are not collected. An analytical separation, which is carried out according to the inventive HPLC methods described herein, typically involves a step of loading less than 20 µg; and preferably, less than 10 µg of sample mixture on the column. An analytical separation may, for example, be performed to identify an unknown solute, to quantify a particular component in a mixture, to control the purity of a compound or molecule, or to assess the quality of a pharmaceutical preparation.

In a preparative isolation, at least one of the components of the sample mixture analyzed is collected as it elutes from the HPLC column. A preparative isolation, which is carried out according to the inventive HPLC methods described herein, generally involves a step of loading less than 100 mg; and preferably between 1 and 100 mg of sample on the column. A preparative isolation may, for example, be performed to purify a particular compound or molecule, or to isolate a fraction of interest from a mixture. Collection of analytes as they emerge from the HPLC column as solution in the mobile phase may be performed by any of the methods known in the art. Automatic fraction collectors are usually very versatile and offer a wide variety of options. They can be operated as a simple fraction collector, where each fraction is the same size and the fraction size is set in terms of time, number of drops, or external events (like counts from a pump), or they can be programmed to respond to an internal peak detector (i.e., to a particular property of the eluant) in order to collect only the analytes of interest. Fraction collectors usually accommodate a wide range of adapter racks and related collection vessels including microliter plates, microcentrifuge tubes, scintillation vials, test tubes, bottles, flasks and vials of different sizes.

Analytes

The inventive methods may be used for analyzing, detecting, separating, isolating, and/or purifying any compound, agent, or molecule that can be loaded on and eluted through a silica gel-based reversed-phase HPLC column. Generally, reversed-phase chromatography is used for the study of non-polar or weakly polar water-soluble molecules; however, certain polar and/or ionic molecules can be analyzed by using more polar bonded phases or such techniques as ion-pair chromatography.

Analytes that may be investigated using the inventive HPLC methods, include, for example, small organic molecules, natural products, and biomolecules such as polypeptides, polynucleotides, and oligonucleotides.

Drug-Candidate Libraries. The inventive HPLC methods may, in particular, find applications in drug discovery, which commonly involves high throughput screening processes on large numbers of samples. Due to the increased utilization of combinatorial methods in the development of pharmaceuticals, much effort has been placed on designing analytical methodologies that are able to rapidly screen, characterize and/or purify large numbers of compounds in the shortest possible time. HPLC-MS is commonly used to confirm the presence and control the purity of potential target compounds and has already proved to be an effective tool to process very large drug-candidate libraries.

Different types of libraries have been generated: chemical libraries, natural product libraries, and combinatorial libraries. Chemical libraries consist of structural analogs of known compounds or compounds that are identified as "hits" or "leads" via natural product screening. Natural product libraries are derived from collections of microorganisms, animals, plants, or marine organisms; they include polyketides, non-ribosomal peptides, and variants (non-naturally occurring) thereof. Combinatorial libraries are composed of large numbers of peptides, oligonucleotides, or other organic compounds. They are relatively easy to prepare by traditional automated synthesis, PCR, cloning or proprietary synthetic methods (for a review of combinatorial chemistry and libraries created therefrom, see, for example, P. L. Myers, Curr. Opin. Biotechnol. 1997, 8: 701–707).

The inventive HPLC methods described herein, that lead to increased column lifetimes and avoid problems of column instability such as those usually encountered under intermediate to high pH aqueous mobile phase conditions, are particularly well suited for high throughput screening, where hundreds or thousands of injections are performed each day. By increasing the column longevity, the inventive HPLC methods decrease the number of times the column has to be changed out over the course of the day, which constitutes a considerable advantage when performing an automated high throughput assay. This, in turn, leads to a significant cut in the overall cost of the analysis.

Polypeptides. The inventive HPLC methods may also be used for analyzing, detecting, separating, isolating and/or purifying polypeptides.

Reversed-phase HPLC has established itself as the method of choice for the separations of peptides. The method is rapid and sensitive; resolution can be excellent; and recovery of peptides and proteins under 60,000 daltons is generally >90%. The method produces highly concentrated fractions of peptides and is also compatible with a wide variety of salts commonly used in protein purification. Reversed-phase HPLC has long played a major role in research, production, and quality control of polypeptide pharmaceuticals, as well as in the development of well-characterized peptide-based biopharmaceuticals, which is an important step for obtaining FDA approval.

The preponderant role of reversed-phase HPLC methods in the analysis and separation of polypeptides results from the diversity of peptide structures. Even closely related peptides typically exhibit subtle conformational differences as well as chemical differences at multiple sites. This remarkable diversity provides means to alter the selectivity and control the resolution in reversed-phase separation of peptides to a much greater extent that is normally possible when separating smaller, simpler molecules.

In reversed-phase HPLC, peaks corresponding to flexible molecules, such as peptides and proteins, are usually broad. Using trifluoroacetic acid (TFA) for ion-pairing is common practice in reversed-phase separation of peptides and proteins. TFA in the mobile phase has the most important effect of improving peak shapes as it overcomes peak broadening and tailing that are believed to result from mixed-mode interactions of peptide molecules having a variety of polar, ionic and hydrophobic sites with hydrophobic bonded phases and residual silanol groups on the silica surface. Trifluoroacetic acid is thought to exert its effects by pairing with positive charges and polar groups on peptides and proteins to mask these sites from polar interactions and bring them to the hydrophobic reversed-phase surface. TFA may similarly mask unreacted silanols. Altering TFA concentration changes reversed-phase selectivity for peptides in subtle ways. These changes can be exploited to optimize separations or increase the information obtained from complex chromatograms, for example, peptide fingerprints.

Reversed-phase HPLC using a gradient of water to acetonitrile with about 0.1% trifluoroacetic acid has been the standard for purification, separation, and characterization of proteins and peptides for nearly two decades. While acetonitrile and methanol are used without problems in analytical separations, preparative isolations of proteins may be performed with less expensive and non-toxic solvents such as ethanol or isopropanol. Ethanol is generally a good choice because it is available in USP grade at reasonable cost; is familiar to the FDA; and is environmentally harmless. Although the organic solvents used in reversed-phase elution may disrupt tertiary structures, many proteins will refold and regain activity when returned to aqueous buffers. Some proteins, especially those with disulfide bridges that help maintain the structure, will either not lose activity or refold very rapidly. For others, proper refolding is often favored by gradual removal of solvent at moderate temperatures.

Gradients in the organic solvent concentration are normally used to obtain sharp peaks and optimum selectivity. Initial organic concentrations range from 1–2% for hydrophilic peptides to 20–40% for large or hydrophobic proteins. While most polypeptides will elute in 70% organic solvent or less, large or hydrophobic proteins (such as membrane proteins and inclusion bodies) may require as high as 85% organic solvent to elute. The gradient slope is normally around 1–2% per minute, however, very shallow gradients (as low as 0.05 to 0.2% per minute) are sometimes used to separate complex mixtures or very similar peptides.

Different ion-pairing agents (i.e., other than trifluoroacetic acid) have been used in the reversed-phase HPLC separations of peptides and proteins. These agents include, acetic acid, sodium and/or ammonium acetate. However, TFA often appears to have the best characteristics for these separations. Its properties as strong ion-pairing agent allow it to complex with these charged biomolecules, increasing their retentivity and minimizing their electrostatic interactions with the HPLC packing material. In preparative separations, TFA may be replaced by acetic acid.

Peptide peaks are sometimes sharper in phosphate buffer than in the presence of TFA because the negative charges on the phosphate molecule interact with basic side chains and increase the rigidity of the peptide. In addition, TFA, which is composed of a less polar end and a more polar end, may cause a different orientation of a peptide relative to the reversed-phase surface than a buffer such as phosphate. The more polar end of TFA is believed to ion-pair with basic side chains, while the less polar end penetrates the reversed-phase, thus facilitating interaction of the basic side chains with the reversed-phase surface. In contrast, phosphate ion pairs with the basic side chain and orients it towards the polar aqueous phase. The difference in orientation causes basic peptides to be retained longer in TFA than in phosphate.

Polypeptides are usually detected by UV absorption at wavelengths between 210 and 220 nm, where the peptide bond absorbs. Higher wavelengths (e.g., 280 nm) are sometimes used to monitor proteins with aromatic residues such as tryptophan.

The mobile phase for use in preparative reversed-phase HPLC should be mild to the polypeptides so as not to irreversibly denature them and be inert to the support. Damage to the support is not only inherently disadvantageous with regards to the HPLC column itself but can also produce toxic by-products which are not acceptable with proteins that might subsequently be used in, for example, pharmaceutical and clinical applications. The inventive HPLC methods, that lead to increased column stability by preventing degradation of the packing material in intermediate to high pH aqueous mobile phases, used in combination with an ion-pairing method, may, therefore, be particularly useful in the preparative separations of proteins.

Polynucleotides and Oligonucleotides. Similarly, the inventive HPLC methods combined with an ion-pairing method, may be used for analyzing, detecting, separating, isolating, and/or purifying polynucleotides and oligonucleotides.

The central role of nucleic acids in biosciences has brought about rapid development of numerous techniques for their isolation, separation, quantitation, and structural analysis. Liquid chromatography (high-performance liquid chromatography in particular) is one technique which can provide rapid analysis and purification of these biomolecules. The size, chemical properties (charge and hydrophobicity) and conformational constraints of nucleic acid molecules can be exploited via the interactions of nucleic acids with reversed-phase solid support. Silica-based reversed-phase chromatography methods perform adequately for separating single-stranded DNA; however, ion-pair chromatography has proved more suited for the analysis and characterization of double-stranded DNA (C. G. Huber and A. Krajete, Anal. Chem. 1999, 71: 3730–3739; A. Apfel et al., Anal. Chem. 1997, 69: 1320–1325).

The analysis of DNA and DNA fragments by ion-pair reversed-phase HPLC may be carried out under non-denaturing, partially denaturing, or fully denaturing conditions. Under non-denaturing conditions, the method provides a means for sequence-independent sizing of DNA fragments of up to 2000 base pairs (C. G. Huber et al., Anal. Chem. 1995, 67: 578–585; K. H. Hecker et al., Biotechniques, 1999, 26: 216–218). Detection of mutations by heteroduplex analysis is possible using partially denaturing conditions (B. Hoogendoorn et al., Hum. Genet. 1999, 104: 89–93; M. C. O'Donovan et al., Genomics, 1998, 52: 44–49), while fully denaturing conditions have been shown to allow the study of single stranded DNA fragments of up to 100 nucleotides (P. J. Oefner, J. Chromatogr. 2000, 739: 345–355) and the analysis of RNA (A. Azarani and K. H. Hecker, Nucleic Acids Res. 2001, 29: E7).

Similarly, the use of oligonucleotides for such applications as primers in sequencing techniques, site-specific mutagenesis, hybridization probes as well as for diagnostic and therapeutic purposes (as antisense drugs) has increased the need for analysis and purification methods for these molecules. Oligonucleotides, which typically contain both negatively charged and neutral portions, may be analyzed by ion-pair reversed-phase HPLC under fully denaturing conditions (C. G. Huber et al., Anal. Biochem. 1993, 212: 351–358) and LC/MS methods have been developed for the characterization of oligonucleotide-based drugs and diagnostic probes (M. Gilar, Anal. Biochem. 2001, 298: 196–206).

Depending on the denaturing conditions desired for a particular chromatographic analysis, the pH of the mobile phase or the temperature of the HPLC column may be varied to achieve optimal separation of polynucleotides. For example, when the temperature is used to effect at least partial denaturation of nucleic acid molecules such as DNA and RNA fragments, the pH of the mobile phase is maintained between 7 and 9. Preferably, the mobile phase is maintained at a pH around 7.5. Alternatively, the pH of the mobile phase may be adjusted to effect at least partial denaturation of the nucleic acid molecules, by addition of either a base (e.g., sodium hydroxide or urea) or an acid (e.g., acetic acid). In such cases, the temperature of the column is kept below about 50° C.

Trialkylammonium salts, such as triethylammonium bicarbonate, appear to be useful as ion-pairing agents in the separation of polynucleotides, while triethylamine acetate has often been added to mobile phase for oligonucleotide reversed-phase chromatography.

Polynucleotide molecules have been shown to be more easily separated when the mobile phase flowing through the HPLC column is substantially free of multivalent cation contaminants (e.g., Fe(III) (or $Fe^{3+}$), Cr(III) (or $Cr^{3+}$), and colloidal metal contaminants). The presence of a multivalent cation binding agent such as EDTA in the mobile phase prevents the adsorption of these biomolecules to the silica.

DNA Fragments. In certain preferred embodiments, the inventive methods are used for analyzing, detecting, separating, isolating, and/or purifying DNA fragments in a sample mixture. Preferably, the additive is a polyfluorinated alcohol. More preferably, the additive is a polyfluorinated alcohol selected from the group consisting of 2,2,2-trifluoroethanol; 1,1,1,3,3,3-hexafluoroisopropanol; and combinations thereof. The mobile phase may further comprise at least one ion-pairing agent, at least one multivalent cation binding agent, and at least one water-soluble solvent. In preferred embodiments, the ion-pairing agent is a trisubstituted ammonium salt, the multivalent cation binding agent is EDTA, and the water-soluble organic solvent is acetonitrile. The mobile phase may be run through the HPLC column using an isocratic elution or a gradient elution. Preferably, a gradient is used.

Compared to conventional reversed-phase techniques used to separate DNA fragments, the inventive HPLC methods present the additional advantage of separating the fragments based on their length rather than on their composition. DNA fragment sizing is, for example, required for quality control of sequencing templates, quantitation and sizing of DNA fragments, assays for the presence of a DNA fragment in genotyping, optimization of PCR conditions, and assessment of quality control of PCR products.

EXAMPLES

The following examples describe certain modes of making and practicing the present invention. However, it should be understood that these examples are for illustrative purposes only and are not meant to limit the scope of the invention.

Materials and Methods

Materials. The pbr 322 Hae III DNA digest was purchased from Sigma-Aldrich (Milwaukee, Wis.). It is supplied at a concentration of 0.5 mg/mL in 10 mM Tris-HCl (pH 7.8), 1 mM EDTA. The DNA digest sample contains 22 fragments ranging from 8 to 587 base pairs (more specifically, fragments of 8, 11, 18, 21, 51, 57, 64, 80, 89, 104, 123, 124, 184, 192, 213, 234, 267, 434, 458, 502, 540 and 587 base pairs are present in the digest).

The 23-mer oligonucleotide, having the sequence 5'-CTT CTC TGA CAAC TGA CAC GTG GC-3' (SEQ ID NO:01), and the 25-mer oligonucleotide, having the sequence 5'-ACC TTC TCT GAC ACT GAC ACG TGG C-3' (SEQ ID NO:02), were purchased from XX-IDT (Coralville, Iowa).

Acetonitrile, 1,1,1,3,3,3-hexafluoroisopropanol (hereafter called hexafluoro-isopropanol), 2,2,2-trifluoroethanol (hereafter called trifluoroethanol), triethylammonium acetate (TEAA), and ethylenediaminetetraacetic acid (EDTA), were of HPLC grade, purchased from Sigma-Aldrich and used without further purification.

High-Performance Liquid Chromatography System. The chromatographic analyses were performed on an Agilent 1100 HPLC system (Agilent Technologies, Palo Alto, Calif.), using Poroshell C18 HPLC columns (Agilent Technologies) and a UV detector set at 254 nm.

Column Aging Method in the Absence of a Fluorinated Additive. The HPLC column was aged over 62 hours by performing a series of 30 minutes chromatographic runs under the following conditions: Injection: 2 μl of water, Mobile phase, solvent A: 0.1 M TEAA/0.1 mM EDTA, pH=7, solvent B: A in 25% acetonitrile; Gradient: 30–80% B in 20 minutes; Flow rate: 0.25 mL/mn; Column temperature: 75° C.

Column Aging Method in the Presence of a Fluorinated Additive. The HPLC column was aged over 62 hours by performing a series of 30 minutes chromatographic runs under the following conditions: Injection: 2 μl of water, Mobile phase, solvent A: 0.1 M TEAA/0.1 mM EDTA/0.08 M hexafluoroisopropanol or trifluoroethanol, pH=7, solvent B: A in 25% acetonitrile; Gradient: 30–80% B in 30 minutes; Flow rate: 0.25 mL/mn; Column temperature: 75° C.

Example 1

Effects of Column Aging on DNA Fragments Separation in the Absence of Fluorinated Additive The goal of the experiment reported herein was to test the effects of column aging on the separation of DNA fragments. A DNA marker (the pbr 322 Hae III DNA digest) was first analyzed by reversed-phase chromatography using a Poroshell C18 HPLC column. The injected DNA sample (2 μL) was eluted at a constant flow rate of 0.25 mL/mn using a gradient composed of two solvents (solvent A: 0.1 M TEAA/0.1 mM EDTA, pH=7, solvent B: A in 25% acetonitrile; where the proportion of B in the mixture was increased from 40 to 80% over a period of 30 minutes). During the chromatographic run, the temperature of the column was kept constant at 50° C. The chromatogram obtained from this first injection is presented in part A of FIG. 1.

The HPLC column was then submitted to a controlled aging process (in the absence of polyfluorinated alcohol) as described above. The unusually high temperature ensured an extreme test of column stability.

62 hours after the first injection, a pbr 322 Hae III DNA digest sample was again analyzed under the same experimental conditions. The chromatogram obtained from this second injection is presented in part B of FIG. 1.

Figure 1B:
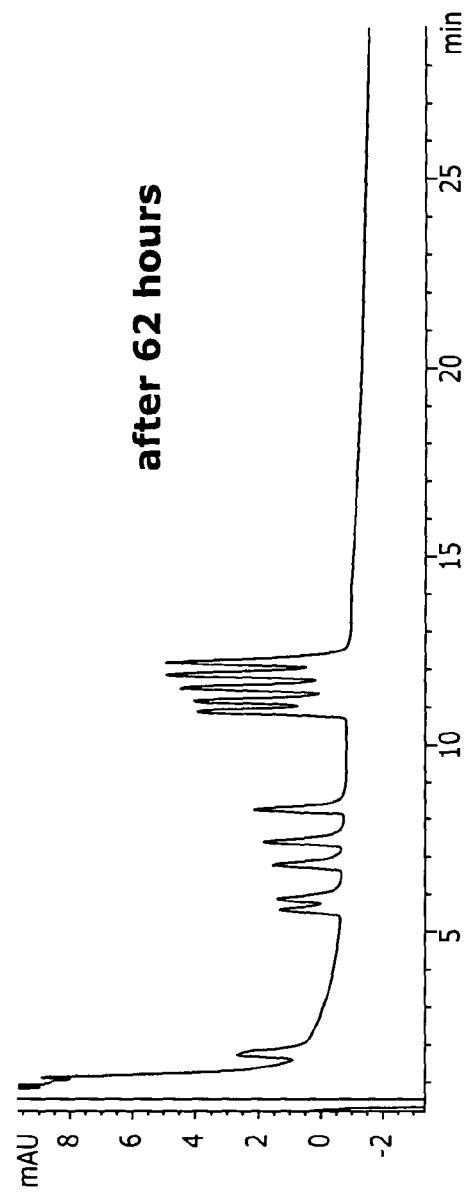

Comparison of parts A and B of FIG. 1 shows that the aged column has lost its ability to separate the different DNA fragments (instead of the 18 peaks observed in FIG. 1A, only 11 peaks are visible in FIG. 1B). In addition to the dramatic shortening of the retention time of all the peaks (e.g., the last group of peaks which are detected 23 to 25 minutes after injection in the first chromatogram, have retention times between 10.5 and 13 minutes in the second analysis). A decrease in the resolution is also observed.

Example 2

Effects of Column Aging on DNA Fragments Separation in the Presence of Hexafluoroisopropanol The goal of the experiment reported herein was to test the effects of adding hexafluoroisopropanol to a mobile phase on column aging. The same DNA marker than that used above (i.e., the pbr 322 Hae III DNA digest) was first analyzed by reversed-phase chromatography using a Poroshell C18 HPLC column in the presence of hexafluoroisopropanol. The injected DNA sample (2 μL) was eluted at a constant flow rate of 0.25 mL/mn using a gradient composed of two solvents (solvent A: 0.1 M TEAA/0.1 mM EDTA/0.08 M hexafluoroisopropanol, pH=7, solvent B: A in 25% acetonitrile; where the proportion of B in the mixture was increased from 60 to 100% over a period of 30 minutes). During the chromatographic run, the temperature of the column was kept at 50° C. The chromatogram obtained from this first injection is presented in part A of FIG. 2.

After this first injection, the column was submitted to a controlled aging process in the presence of hexafluoroisopropanol as described above.

62 hours after the first injection, a pbr 322 Hae III DNA digest sample was again analyzed under the same experimental conditions. The chromatogram obtained from this second injection is presented in part B of FIG. 2.

Figure 2A:
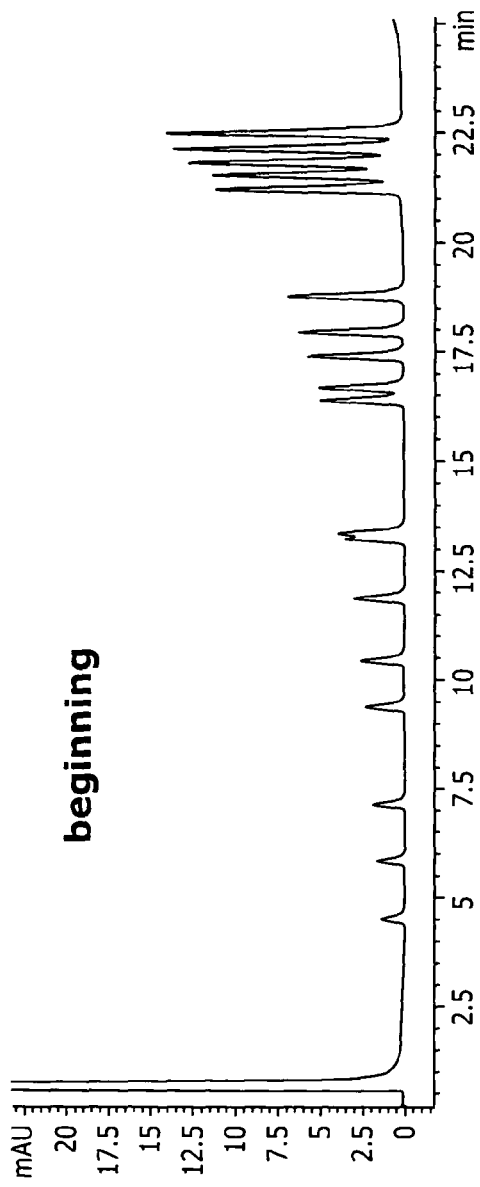
FIG. 2 illustrates the effects of column aging on the separation of DNA fragments when 1,1,1,3,3,3-hexafluoroisopropanol is present in the mobile phase. Part A of FIG. 2 shows a chromatogram obtained by injecting a pbr 322 Hae III DNA digest sample (2 μL) on a Poroshell C18 HPLC column. The conditions of the chromatographic run were as follows: Mobile phase, solvent A: 0.1 M TEAA/0.1 mM EDTA/0.08 M hexafluoroisopropanol, pH=7, solvent B: A in 25% acetonitrile; Gradient: 60–100% B in 30 minutes; Flow rate: 0.25 mL/mn; Column temperature: 50° C. Part B of FIG. 2 shows a chromatogram obtained under the same experimental conditions 62 hours after that displayed in part A. Between the two injections of DNA digest, the column was "aged" in a controlled manner in the presence of 1,1,1,3,3,3-hexafluoroisopropanol as described in Example 2.
Figure 2B:
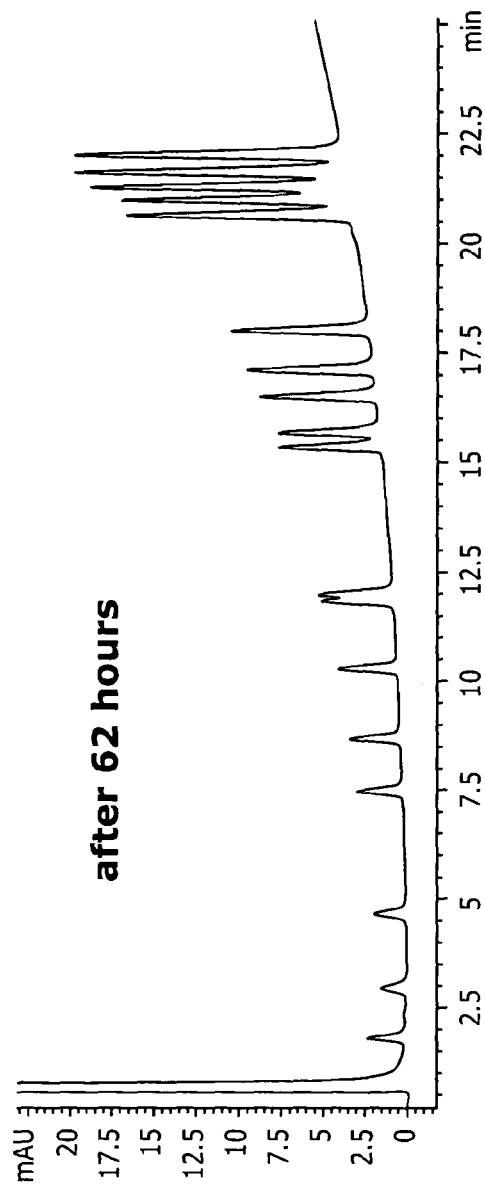

Comparison of parts A and B of FIG. 2 shows that the column aged in the presence of hexafluoroisopropanol has retained its ability to resolve the 18 DNA fragments. A slight decrease (of 1 to 3 min.) in the retention time is observed for all the peaks in FIG. 2B compared to FIG. 2A, but the resolution is not affected.

Example 3

Effects of Column Aging on DNA Fragments Separation in the Presence of Trifluoroethanol The experiment described in Example 2 was performed using trifluoroethanol instead of hexafluoroisopropanol.

Figure 3A:
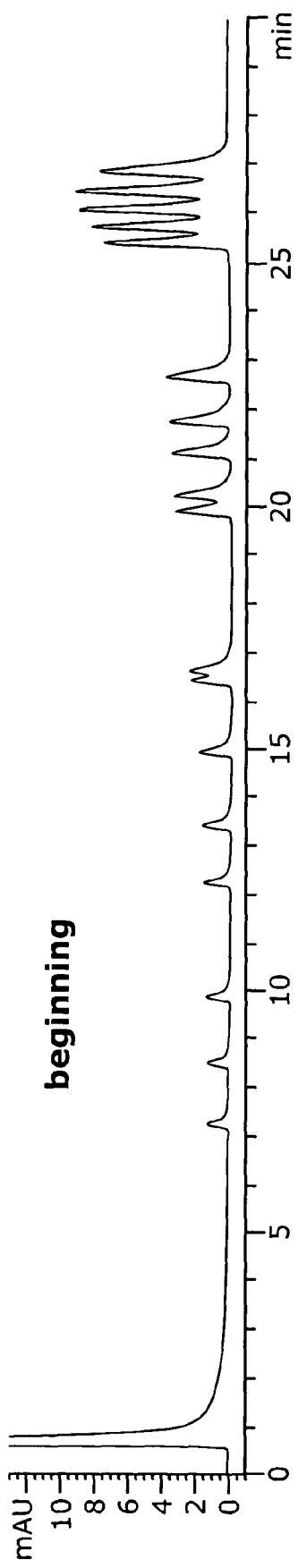
FIG. 3 illustrates the effects of column aging on the separation of DNA fragments when 2,2,2-trifluoroethanol is present in the mobile phase. Part A of FIG. 3 shows a chromatogram obtained by injecting a pbr 322 Hae III DNA digest sample (2 μL) on a Poroshell C18 HPLC column. The conditions of the chromatographic run were as follows: Mobile phase, solvent A: 0.1 M TEAA/0.1 mM EDTA/0.08 M trifluoroethanol, pH=7, solvent B: A in 25% acetonitrile; Gradient: 60–100% B in 30 minutes; Flow rate: 0.25 mL/mn; Column temperature: 50° C. Part B of FIG. 3 shows a chromatogram obtained under the same experimental conditions 62 hours after that displayed in part A. Between the two injections of DNA digest, the column was "aged" in a controlled manner in the presence of trifluoroethanol as described in Example 3.
Figure 3B:
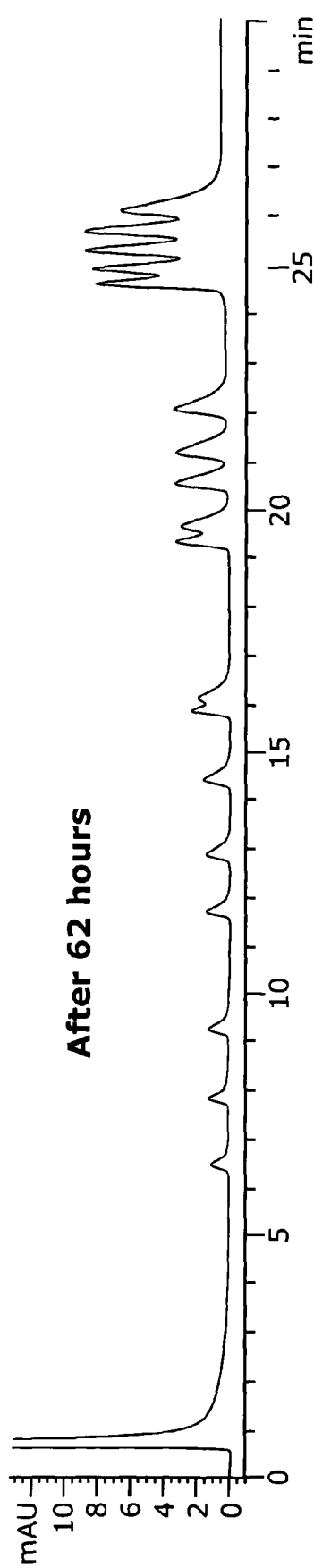

The chromatograms obtained before and after the step of aging the HPLC column in the presence of trifluoroethanol in the mobile phase are presented in parts A and B of FIG. 3, respectively. Here again, the aging process carried out in the presence of trifluoroethanol has not altered the HPLC column's ability to separate the 18 DNA fragments. A slight decrease in retention time is observed for all the peaks in FIG. 3B compared to FIG. 3A, but the resolution is almost not affected.

Example 4

Effects of the Presence of Hexafluoroisopropanol on the Separation of Single Strain Oligonucleotides The goal of the experiment reported herein was to test the effects of the presence of a polyfluorinated alcohol in the mobile phase on the separation of two single strand oligonucleotides (a 23-mer and a 25-mer). A mixture of the two oligonucleotides was first analyzed by reversed-phase chromatography using a Poroshell C18 HPLC column, by elution at a constant flow rate of 0.5 mL/mn using a gradient composed of two solvents (solvent A: 0.1 M TEAA/0.1 mM EDTA, pH=7, solvent B: A in 25% acetonitrile; where the proportion of B in the mixture was increased from 20 to 55% over a period of 8 minutes). During the chromatographic run, the temperature of the column was kept constant at 50° C. The chromatogram obtained from this first injection is presented in part B of FIG. 4. It clearly shows that (1) this conventional HPLC method does not lead to a good separation of the two oligonucleotides, and (2) the retention of the analytes in the column does not increase with the size of the oligonucleotides (as the 25-mer has a shorter retention time than the 23-mer).

Figure 4A:
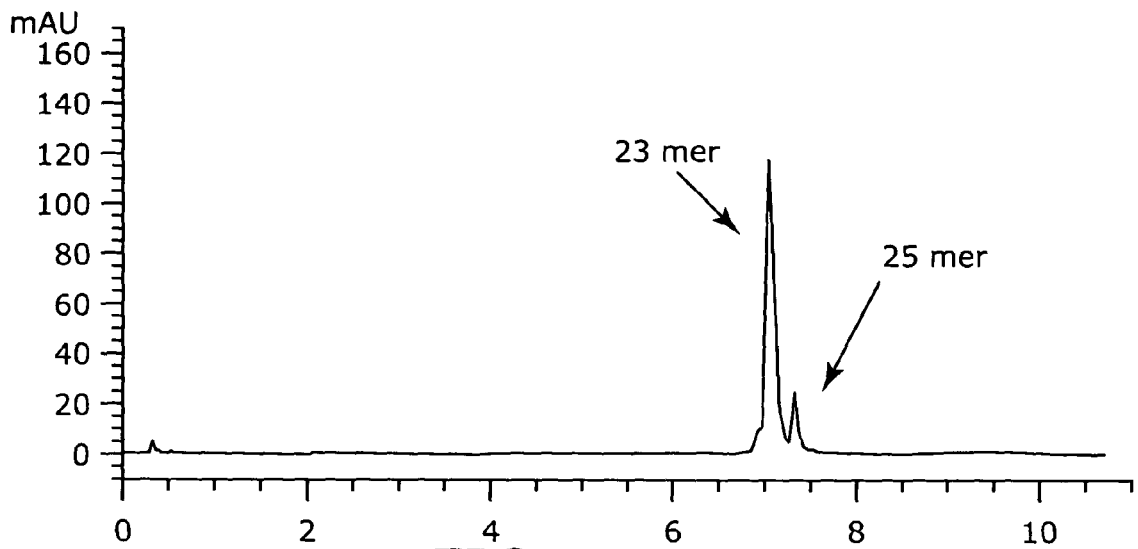
FIG. 4 illustrates the effects of the presence of 1,1,1,3,3,3-trifluoroisopropanol in the mobile phase on the separation of two single strain oligonucleotides (a 23-mer and a 25-mer). Part A of FIG. 4 shows a chromatogram obtained by injecting a mixture of the two oligonucleotides on a Poroshell C18 HPLC column. The conditions of the chromatographic run were as follows: Mobile phase, solvent A: 0.1 M TEAA/0.1 mM EDTA, pH=7, solvent B: A in 25% acetonitrile; Gradient: 20–55% B in 5 minutes; Flow rate: 0.5 mL/mn; Column temperature: 20° C. The chromatogram presented in part B of FIG. 4 was obtained under the same experimental conditions with the exception that the column temperature was 50° C. instead of 20° C.; and the gradient was: 20–55% B in 8 minutes. Part C of FIG. 4 shows a chromatogram obtained as in part B except that solvent A was 0.1 M TEAA/0.1 mM EDTA/0.08 M hexafluoroisopropanol.
Figure 4B:
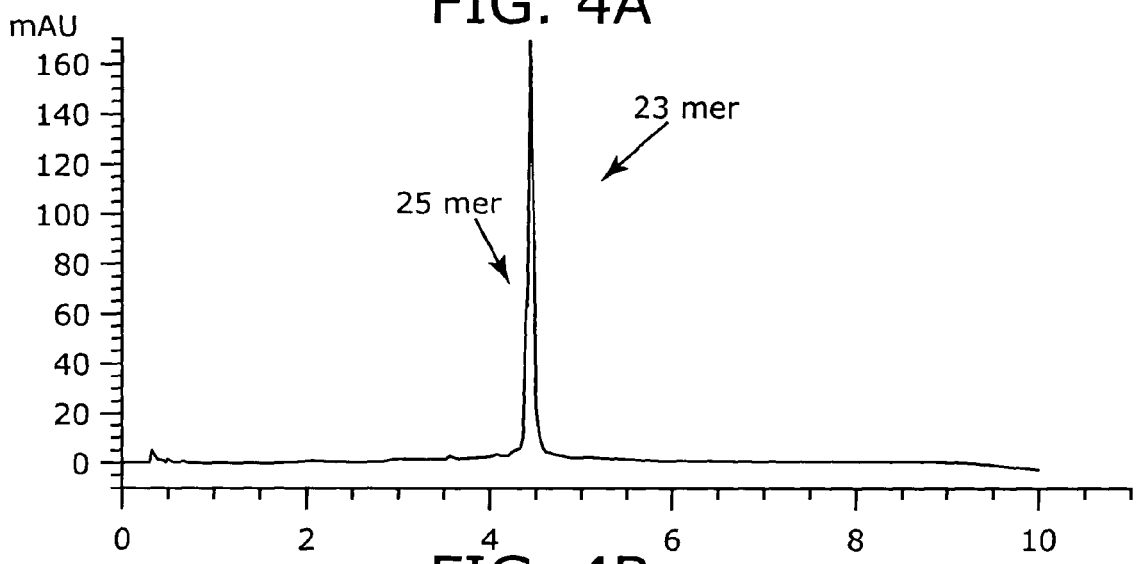
Figure 4C:
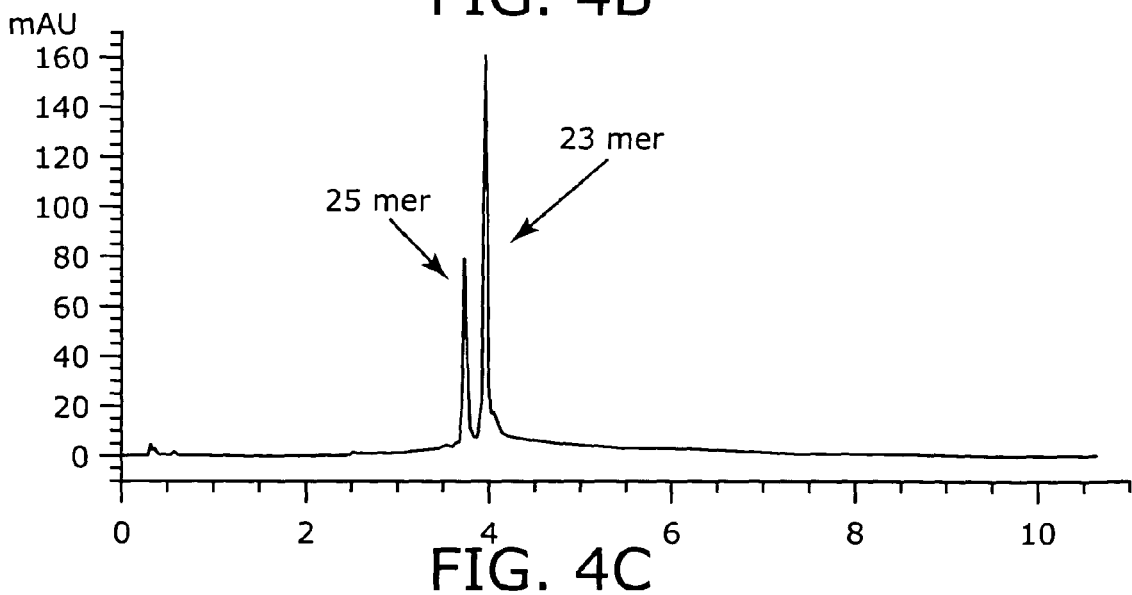

As shown by the chromatogram presented in part C of FIG. 4 and obtained under experimental conditions identical to those used in part B except that the temperature of the column was 20° C. instead of 50° C., this effect is even more significant at lower temperature.

The mixture of oligonucleotides was then analyzed using the same experimental conditions than those used in the first injection, except that solvent A was: 0.1 M TEAA/0.1 mM EDTA/0.08 M hexafluoroisopropanol. The chromatogram obtained for this third injection is presented in part A of FIG. 4. In the presence of hexafluoroisopropanol in the mobile phase, a good separation of the two oligonucleotides is obtained and the retention of the oligonucleotides in the column increases as a function of size.

What is claimed is:

1. A method for increasing column lifetime for a HPLC column packed with a superficially porous silica-based reversed-phase support, the method comprising:

eluting the HPLC column, which is packed with a superficially porous silica-based reversed-phase support and loaded with a sample mixture comprising at least two components, with an aqueous mobile phase comprising between 0.5 and 10% by volume of at least one neutral, polar, fluorinated organic compound; wherein the presence of the neutral, polar, fluorinated organic compound in the aqueous mobile phase leads to an increased column lifetime, as compared with the lifetime observed in the absence of the neutral, polar, fluorinated organic compound, all other conditions being equal.

2. The method of claim 1, wherein the presence of the neutral, polar, fluorinated organic compound in the mobile phase leads to a higher retention of at least one component of the sample mixture as compared with the retention observed for the same component of the sample mixture in the absence of the neutral, polar, fluorinated organic compound, all other conditions being equal.

3. A method according to claim 1 or 2, further comprising detecting at least one of the components of the sample mixture as it elutes from the column as a solution in the mobile phase.

4. A method according to claim 3, wherein the method is a method for analysis of at least one component of the sample mixture.

5. A method according to claim 1 or 2, further comprising collecting at least one component of the sample mixture in a distinct fraction as it emerges from the column as a solution in the mobile phase.

6. A method according to claim 4, wherein the method is a method for preparative isolation of at least one component of the sample mixture.

7. A method according to claim 1, wherein the neutral, polar, fluorinated organic compound is a polyfluorinated alcohol.

8. A method according to claim 7, wherein the polyfluorinated alcohol is selected from the group consisting of 2,2,2-trifluoroethanol; 1,1,1,3,3,3-hexafluoroisopropanol; and combinations thereof.

9. A method according to claim 7, wherein aqueous mobile phase comprises between 0.5 and 2% by volume of a polyfluorinated alcohol.

10. A method according to claim 1 or 2, wherein the mobile phase has a pH between 2 and 11.

11. A method according to claim 1 or 2, wherein the mobile phase has a pH between 6 and 8.

12. A method according to claim 1 or 2, wherein the mobile phase further comprises a modifier selected from the group consisting of a buffering agent, an ion-pairing agent, a multivalent cation binding agent, a surfactant, a water-soluble organic solvent, and combinations thereof.

13. A method according to claim 1 or 2, wherein the HPLC column is run using an isocratic elution.

14. A method according to claim 1 or 2, wherein the HPLC column is run using a gradient elution.

15. A method according to claim 1 or 2, wherein the components of the mixture are polynucleotides.

16. A method according to claim 1, wherein the mobile phase additionally comprises an ion-pairing agent.

17. A method according to claim 1, wherein the elution of the HPLC column is performed at a temperature between 50° C. and 90° C.

18. A method according to claim 1, wherein the superficially porous silica-based reversed-phase support is derivatized with C4, C8, C18, phenyl or cyano moieties.

19. A method for improving resolution of sample mixture components by increasing retention of at least one component of a sample mixture comprising at least two components, the method comprising:

eluting a HPLC column, which is packed with a superficially porous silica-based reversed-phase support and loaded with a sample mixture comprising at least two components, with an aqueous mobile phase comprising:

between 0.5 to 10% by volume of an additive comprising at least one neutral, polar, fluorinated organic compound; and wherein the presence of the neutral, polar, fluorinated organic compound in the aqueous mobile phase leads to a higher retention of at least one component of the mixture as compared with the retention observed for the same component of the mixture in the absence of the neutral, polar, fluorinated organic compound, all other conditions being equal.

20. The method of claim 19, wherein the presence of the neutral, polar, fluorinated organic compound in the mobile phase leads to an increased column lifetime, as compared with the lifetime observed in the absence of the neutral, polar, fluorinated organic compound, all conditions being equal.

21. A method according to claim 19, wherein the fluorinated organic modifier is a polyfluorinated alcohol.

22. A method according to claim 21, wherein the polyfluorinated alcohol is selected from the group consisting of 2,2,2-trifluoroethanol; 1,1,1,3,3,3-hexafluoroisopropanol; and combinations thereof.

23. A method according to claim 19, wherein the components of the mixture are polynucleotides.

24. A method according to claim 19, wherein the mobile phase additionally comprises an ion-pairing agent.

25. A method according to claim 19, wherein the elution of the HPLC column is performed at a temperature between 50° C. and 90° C.

26. A method according to claim 19, wherein the superficially porous silica-based reversed-phase support is derivatized with C4, C8, C18, phenyl or cyano moieties.

* * * * *